United States Patent
Tsui

(10) Patent No.: US 10,384,012 B2
(45) Date of Patent: Aug. 20, 2019

(54) DEVICES AND METHODS FOR DELIVERING PARTICLES

(71) Applicant: Powder Pharmaceuticals Incorporated, Hong Kong (CN)

(72) Inventor: Victor K. Tsui, Millbrae, CA (US)

(73) Assignee: Powder Pharmaceuticals Incorporated, Hong Kong (CN)

( * ) Notice: Subject to any disclaimer, the term of this patent is extended or adjusted under 35 U.S.C. 154(b) by 0 days.

(21) Appl. No.: 15/077,753

(22) Filed: Mar. 22, 2016

(65) Prior Publication Data

US 2016/0199580 A1   Jul. 14, 2016

Related U.S. Application Data

(60) Division of application No. 14/869,670, filed on Sep. 29, 2015, now Pat. No. 9,370,622, which is a continuation-in-part of application No. PCT/US2015/017816, filed on Feb. 26, 2015.

(60) Provisional application No. 61/945,021, filed on Feb. 26, 2014.

(51) Int. Cl.
*A61M 5/30*   (2006.01)
*A61M 5/20*   (2006.01)

(52) U.S. Cl.
CPC ........ *A61M 5/3015* (2013.01); *A61M 5/2053* (2013.01); *A61M 5/30* (2013.01); *A61M 5/3007* (2013.01); *A61M 2005/208* (2013.01); *A61M 2205/42* (2013.01)

(58) Field of Classification Search
CPC ............... A61M 5/30; A61M 5/3007; A61M 2005/3022; A61M 5/3015
See application file for complete search history.

(56) References Cited

U.S. PATENT DOCUMENTS

| | | | |
|---|---|---|---|
| 2,680,439 A | 6/1954 | Sutermeister | |
| 4,427,743 A | 1/1984 | Katsuki et al. | |
| 4,913,699 A * | 4/1990 | Parsons | A61J 1/2096 604/68 |

(Continued)

FOREIGN PATENT DOCUMENTS

| | | |
|---|---|---|
| CN | 1951510 | 4/2007 |
| CN | 101466423 | 6/2009 |

(Continued)

OTHER PUBLICATIONS

E.I. du Pont de Nemours and Company, Elvax Resins Product Data Sheet, Aug. 8, 2010, E.I. du Pont de Nemours and Company.*

(Continued)

*Primary Examiner* — William R Carpenter
(74) *Attorney, Agent, or Firm* — Levine Bagade Han LLP

(57) ABSTRACT

Systems, devices, and methods for delivering therapeutic particles are disclosed. In one variation, a device for delivering particles includes a gas supply configured for supplying gas under pressure, a particle cassette comprising the particles, a cassette housing, and a cassette membrane. The cassette housing can comprise an Ethylene Vinyl Acetate (EVA) copolymer of 18% to 28% by weight of Vinyl Acetate (VA). The device can also include a safety interlock to prevent or minimize the risk that the device will be unintentionally activated. The device can also have a silencer.

19 Claims, 24 Drawing Sheets

(56) References Cited

U.S. PATENT DOCUMENTS

| | | | |
|---|---|---|---|
| 4,983,171 A * | 1/1991 | Schirmer | A61F 5/445 604/332 |
| 5,360,796 A | 11/1994 | Hansen et al. | |
| 5,472,021 A * | 12/1995 | Tsao | B65D 41/32 141/1 |
| 5,503,627 A | 4/1996 | McKinnon et al. | |
| 5,630,796 A * | 5/1997 | Bellhouse | A61M 5/3015 604/518 |
| 5,670,756 A | 9/1997 | Ohtaka et al. | |
| 5,899,880 A | 5/1999 | Bellhouse et al. | |
| 6,004,286 A * | 12/1999 | Bellhouse | A61M 5/3015 604/140 |
| 6,053,889 A | 4/2000 | Heinzen et al. | |
| 6,210,359 B1 * | 4/2001 | Patel | A61M 5/30 604/68 |
| 6,328,714 B1 | 12/2001 | Bellhouse et al. | |
| 6,475,181 B1 | 11/2002 | Potter et al. | |
| 6,797,737 B1 | 9/2004 | Hsu et al. | |
| 6,849,060 B1 | 2/2005 | Brooks et al. | |
| 8,257,308 B2 | 9/2012 | Bianchi et al. | |
| 9,370,622 B2 | 6/2016 | Tsui | |
| 2002/0091353 A1 * | 7/2002 | Bellhouse | A61M 5/3015 604/68 |
| 2003/0019558 A1 * | 1/2003 | Smith | A61M 5/3015 156/61 |
| 2004/0215135 A1 | 10/2004 | Sheldrake et al. | |
| 2004/0255447 A1 | 12/2004 | Kendall et al. | |
| 2005/0010168 A1 * | 1/2005 | Kendall | A61M 5/3015 604/70 |
| 2006/0112998 A1 | 6/2006 | Smith | |
| 2008/0038356 A1 * | 2/2008 | Maa | A61K 9/0021 424/489 |
| 2008/0148928 A1 | 6/2008 | McClellan | |
| 2010/0121262 A1 | 5/2010 | Bates et al. | |
| 2010/0298767 A1 * | 11/2010 | Bates | A61M 5/2459 604/72 |
| 2011/0045088 A1 | 2/2011 | Tsutsui et al. | |
| 2013/0062366 A1 | 3/2013 | Tansey | |
| 2013/0245544 A1 | 9/2013 | de Juan et al. | |
| 2014/0118827 A1 | 5/2014 | Zhang et al. | |
| 2016/0018178 A1 | 1/2016 | Johansen | |
| 2016/0022910 A1 | 1/2016 | Tsui | |
| 2016/0022911 A1 | 1/2016 | Tsui | |
| 2016/0038681 A1 | 2/2016 | Tsui | |

FOREIGN PATENT DOCUMENTS

| | | |
|---|---|---|
| EP | 0888790 | 1/1999 |
| GB | 1575113 | 9/1980 |
| JP | 2004-536574 | 12/2004 |
| JP | 2004-536675 | 12/2004 |
| JP | 2007-532277 | 11/2007 |
| JP | 2009-539456 | 11/2009 |
| WO | WO 2000/044421 | 8/2000 |
| WO | WO 2015/130961 | 9/2015 |

OTHER PUBLICATIONS

Stanton et al., Angiogenesis Assays—A critical appraisal of current techniques, 2006 John Wiley & Sons Ltd, p. 210-211.*

DuPont Elvax EVA resins for Adhesives, Sealants and Wax Blends, http://www.dupont.com//content/dam/dupont/products-and-services/packaging-materials-and-solutions/packaging-materials-and-solutions-landing/documents/elvax adhesives wax blends.pdf, 2012, accessed on Aug. 17, 2015.*

McKeen, Laurence, Film Properties of Plastics and Elastomers, 2012, Elsevier Inc., Third Edition, 219-223.*

E.I. du Pont de Nemours and Company, Elvax Resins Product Data Sheet, Aug. 8, 2010.

Stanton et al., *Angiogenesis Assays—A critical appraisal of current techniques*, John Wiley & Sons Ltd, pp. 210-211, 2006.

U.S. Appl. No. 14/869,670, filed Sep. 29, 2015.

U.S. Appl. No. 14/873,028, filed Oct. 1, 2015.

U.S. Appl. No. 14/873,054, filed Oct. 1, 2015.

Wittcoff et al., Industrial Organic Chemicals, Second Edition, pp. 110 and 277, Johney Wiley & Sons, 2004, Hoboken, NJ.

* cited by examiner

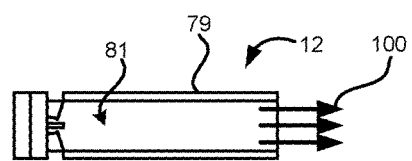
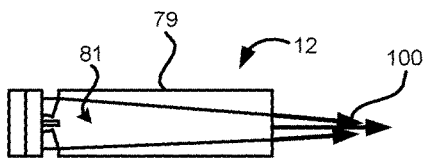
Figure 7c    Figure 7d
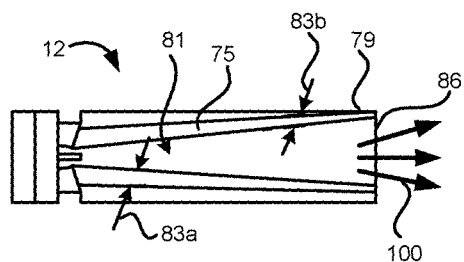
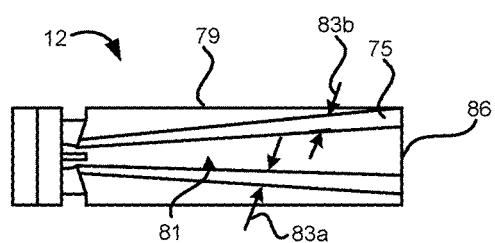
Figure 7e    Figure 7f
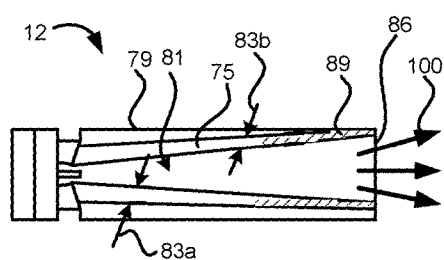
Figure 7g

DEVICES AND METHODS FOR DELIVERING PARTICLES

CROSS-REFERENCE TO RELATED APPLICATIONS

This application is a divisional application of U.S. patent application Ser. No. 14/869,670 filed on Sep. 29, 2015, which is a continuation-in-part application of and claims the benefit of priority to International Application No. PCT/US2015/017816 filed on Feb. 26, 2015, which claims the benefit of priority to U.S. Provisional Application No. 61/945,021, filed on Feb. 26, 2014, the contents of which are incorporated herein by reference in their entirety.

BACKGROUND

The ability to deliver pharmaceuticals or other therapeutics through skin (transdermal) or other organ layers can provide many advantages over oral or parenteral delivery techniques. In particular, transdermal delivery can provide a safe, convenient and noninvasive alternative to traditional drug administration systems, conveniently avoiding the major problems associated with oral delivery (e.g. variable rates of absorption and metabolism, gastrointestinal irritation and/or bitter or unpleasant drug tastes) or parenteral delivery (e.g. needle pain, the risk of introducing infection to treated individuals, the risk of contamination or infection of health care workers caused by accidental needle-sticks and the disposal of used needles). In addition, transdermal delivery can afford a high degree of control over blood concentrations of administered pharmaceuticals.

Traditional needleless syringes are known that deliver therapeutic particles entrained in a supersonic gas flow. Such traditional needleless syringes can be used for transdermal delivery of powdered drug compounds and compositions, for delivery of genetic material into living cells (e.g. gene therapy), and for the delivery of biopharmaceuticals to skin, eye, muscle, blood or lymph. Traditional needleless syringes can also be used in conjunction with surgery to deliver drugs and biologics to organ surfaces, solid tumors, and/or to surgical cavities (e.g. tumor beds or cavities after tumor resection). In theory, practically any therapeutic agent that can be prepared in a substantially solid, particulate form can be safely and easily delivered using such devices.

However, traditional needleless syringes often deliver therapeutic particles at a large range of velocities with potentially non-uniform spatial distribution across a target treatment surface. Differences in particle velocity may make it difficult to deliver high-potency powdered drugs, vaccines, etc. to specific target layers underneath the target treatment surface. Furthermore, such non-uniform spatial distribution may cause further complications with the efficacy of such therapeutics after delivery. In addition, flow considerations inside traditional needleless syringes may limit the maximum treatment surface area over which the therapeutic particles may be spread, thereby limiting the maximum particle payload size.

Additionally, traditional needleless syringes often produce a loud sound when actuated, which can scare patients such as small children, thereby defeating the purpose of choosing a needleless syringe over a needled-syringe. Therefore, a device, system, and/or method is needed for quietly and uniformly delivering particulate therapeutics through a patient's skin or other organ layer over a larger target treatment surface. By uniformly delivering such particulates over a larger treatment surface, therapeutic payloads with larger particulate volumes can be delivered.

SUMMARY

Devices, systems, and methods for delivering therapeutics in particulate or powdered form are disclosed. A device is disclosed for delivering particles. The device can have a gas supply and a particle cassette having a cassette housing and a cassette membrane for storing the particles. The cassette housing can be made of an Ethylene Vinyl Acetate (EVA) copolymer of 18% to 28% Vinyl Acetate (VA). The gas supply can be configured to supply gas under pressure to deliver the particles by rupturing the cassette membrane.

The cassette housing can have a particle reservoir having an inner diameter from 5.0 mm to 7.0 mm. The cassette housing can also have a particle reservoir having an inner diameter from 5.8 mm to 6.5 mm. The cassette membrane can be made of polycarbonate. The cassette membrane can be between 10 to 30 microns thick. The cassette housing can be made of an EVA copolymer between 18% to 20% VA.

The device can have a trigger and a safety interlock configured to impede actuation of the trigger when the safety interlock is engaged. The device can have a silencer cover and a silencer packing material. The cassette housing can be made of an EVA copolymer of 18% VA. The cassette housing can have a male cassette part and a female cassette part and a piece of the cassette membrane can cover a first cassette port of the male cassette part and another piece of the cassette membrane can cover a second cassette port of the female cassette part.

Another variation of the device is disclosed for delivering particles. The device can have a gas supply configured to supply gas under pressure, a particle cassette having a cassette housing and a cassette membrane for storing the particles, wherein the cassette housing comprises an EVA copolymer of 18% to 28% VA, a trigger, and a disengageable safety interlock. A portion of the case can be the disengageable safety interlock.

The cassette membrane can be 10 to 30 microns thick and can be made of polycarbonate. The disengageable safety interlock can be configured to impede actuation of the trigger. The device can comprise a silencer cover and a silencer packing material.

A method is disclosed for delivering particles. The method can include storing the particles in a particle cassette having a cassette housing and a cassette membrane, wherein the cassette housing comprises an EVA copolymer of 18% to 28% VA, delivering pressurized gas to the exterior of the particle cassette, rupturing the particle cassette with the pressurized gas, and accelerating the particles out of the particle cassette with the pressurized gas.

In one variation, greater than 40% of the particles can be delivered by the pressurized gas. In another variation, greater than 70% of the particles can be delivered by the pressurized gas. In yet another variation, between 40-85% of the particles can be delivered by the pressurized gas. In additional variations, between 40-70% of the particles can be delivered by the pressurized gas. In even more variations, between 60-85% of the particles can be delivered by the pressurized gas. The cassette membrane can comprise polycarbonate. The cassette membrane can be 10 to 30 microns thick. The method can include disengaging a safety interlock. The method can include accelerating the particles out of the particle cassette with the pressurized gas through a silencer.

Another variation of the device for delivering particles is disclosed. The device can have a pressurized gas supply storing a pressurized gas, a trigger having a trigger top and a trigger pin, a disengageable safety interlock configured to impede actuation of the trigger, a gas flow passageway, a delivery port, and a particle cassette storing the particles. The particle cassette can be positioned in the gas flow passageway between the pressurized gas supply and the delivery port.

The safety interlock can be fixed to the case. The case can be translatable with respect to the trigger. The case can be in a first position with respect to the trigger and the safety interlock can be configured to impede actuation of the trigger. The safety interlock can also engageably fit into the trigger to prevent actuation of the trigger.

The case can be in a second position with respect to the trigger and the safety interlock can be configured to allow actuation of the trigger. When the trigger is translatable with respect to the safety interlock and when the trigger is in a first position with respect to the safety interlock, the safety interlock can impede actuation of the trigger. When the trigger is in a second position with respect to the safety interlock, the trigger can be free to actuate.

At least part of the safety interlock can be removably attached to the case. At least a portion of the safety interlock can be inside at least a portion of the trigger top when the device is in a locked position. The trigger can be configured to break a portion of the gas supply when the trigger is actuated. The device can have a silencer having a silencer cover and a silencer packing material. The trigger can be configured to translate a removably attached cover on the gas supply when the trigger is actuated. The safety interlock can comprise a triangular impeding element.

The particles can be a powdered form of a therapeutic agent. The therapeutic agent can be an anesthetic.

Another variation of the device for delivering particles is disclosed. The device can include a pressurized gas supply storing a pressurized gas, a trigger having a trigger top and a trigger pin, a case having a disengageable safety interlock configured to impede actuation of the trigger, a gas flow passageway, a delivery port, and a particle cassette.

The particle cassette can contain the particles. The particle cassette can be positioned in the gas flow passageway between the gas supply and the delivery port. A portion of the particle cassette can be made of an EVA copolymer of 18% to 28% VA. The device can have a silencer having a silencer cover and a silencer packing material.

Another variation of a method for delivering particles is disclosed. The method can include disengaging a safety interlock on a delivery device. The delivery device can have a trigger, the safety interlock, a gas supply, and the particles. The method can also include activating the trigger by releasing a pressurized gas from the gas supply, channeling the pressurized gas toward the particles, and accelerating the particles to a treatment surface. The delivery device can accelerate the particles by delivering an accelerating force to the particles.

The delivery device can have a case and the safety interlock can be coupled to the case. Disengaging the safety interlock can involve moving the case relative to the trigger. The safety interlock can have an impeding element and the impeding element can extend from the case parallel to a longitudinal axis of the case. The impeding element can be located inside the trigger. Disengaging the safety interlock can include breaking an impeding element. Disengaging the safety interlock can also include removing the impeding element from the inside of the trigger.

The safety interlock can also be contiguous with and extend from the case. The case can be separably attached to an impeding element. Disengaging the safety interlock can include separating the impeding element from the case.

The delivery device can have a particle cassette and a cassette membrane for storing the particles. The pressurized gas can breach the cassette membrane to deliver the particles out of the particle cassette and into a gas flow passageway leading to the treatment surface. The particle cassette can have a cassette housing and the cassette membrane can be coupled to the cassette housing. The cassette housing can be made of an EVA copolymer of 18% to 28% VA. The method can include accelerating the particles to the treatment surface through a silencer comprising a silencer cover and a silencer packing material.

Another variation of the device for delivering particles is disclosed. The device can have a pressurized gas supply, a gas flow passageway defined by a device segment, a particle cassette, a first silencer component, and a second silencer component.

The first silencer component can radially surround an outer surface of the device segment. The first silencer component can also radially surround an inner surface of the device segment. The first silencer component can be a silencer packing material. The silencer packing material can be made of foam. The foam can be made of porous polyurethane. The first silencer component can be a coating. The coating can be made of polyurethane. The coating can be formed by double-injection molding.

The second silencer component can radially surround the device segment. The second silencer component can define at least a length of the gas flow passageway. The second silencer component can be a silencer cover. The second silencer component can radially surround the first silencer component.

The first silencer component can also radially surround an inner surface of the second silencer component. The pressurized gas supply can deliver a pressurized gas between 10 to 60 bar of pressure through the gas flow passageway. The pressurized gas can also deliver the particles from the particle cassette through the gas flow passageway. The device can comprise a cassette housing for storing the particles and wherein the cassette housing can comprise EVA copolymer of 18% to 28% VA. The device can comprise a disengageable safety interlock.

The device can have a nozzle. At least a length of the gas flow passageway can extend through the nozzle. At least a portion of the nozzle can extend radially outward in a downstream direction of the gas flow passageway. The first silencer component can radially surround an outer surface of the nozzle.

Another variation of the device for delivering particles is disclosed. The device can have a silencer cover, a silencer packing material, a gas flow passageway defined by a device segment, a particle cassette having a cassette housing storing the particles, and a pressurized gas supply. The pressurized gas supply can be configured to deliver the particles through the gas flow passageway using pressurized gas. The cassette housing can be made of an EVA copolymer of 18% to 28% VA.

The silencer packing material can radially surround an outer surface of the device segment. The silencer packing material can also radially surround an inner surface of the device segment. The silencer cover can define at least a length of the gas flow passageway. The silencer cover can surround the silencer packing material. The device can have a disengageable safety interlock.

Another variation of the device for delivering particles is disclosed. The device can have a silencer, a trigger, a disengageable safety interlock configured to impede actuation of the trigger, a gas flow passageway defined by a device segment, and a pressurized gas supply. The pressurized gas supply can be configured to deliver the particles through the gas flow passageway using pressurized gas when the trigger is actuated.

The device can also have a case. A portion of the case can be the disengageable safety interlock. The silencer can surround an outer surface of the device segment. The silencer can surround an inner surface and an outer surface of the device segment. The silencer can have a polyurethane foam coating.

The device can have a particle cassette having a cassette housing for storing the particles. The cassette housing can be made of an EVA copolymer of 18% to 28% VA.

BRIEF DESCRIPTION OF THE DRAWINGS

FIG. 1*b* is a cross-sectional view of the delivery device taken along cross-section A-A of FIG. 1*a*.

FIG. 2*b* is a cross-sectional view of a variation of the inner housing taken along cross-section C-C of FIG. 2*a*.

FIG. 3*b* is a cross-sectional view of a variation of the gas supply taken along cross-section D-D of FIG. 3*a*.

FIG. 4*b* is a cross-sectional view of a variation of the compliant ball spacer taken along cross-section E-E of FIG. 4*a*.

FIG. 5*b* is a cross-sectional view of a variation of the filter taken along cross-section L-L of FIG. 5*a*.

FIG. 6*b* is a cross-sectional view of a variation of the expansion chamber taken along cross-section F-F of FIG. 6*a*.

FIG. 7*b* is a cross-sectional view of a variation of the nozzle taken along cross-section G-G of FIG. 7*a*.

FIGS. 7*c* through 7*g* illustrate variations of the nozzle.

FIG. 8*b* a cross-sectional view of a variation of the retainer taken along cross-section H-H of FIG. 8*a*.

FIG. 9*b* is a cross-sectional view of a variation of the silencer cover taken along cross-section M-M of FIG. 9*a*.

FIG. 10 illustrates a cross-sectional view of a silencer.

FIG. 11 is a perspective view of a spring of the delivery device.

FIG. 12*a* illustrates a variation of a cover.

FIG. 12*b* illustrates a cross-sectional view of a variation of the cover taken along cross-section V-V of FIG. 12*a*.

FIG. 13*a* illustrates cross-sectional view of a variation of a trigger.

FIG. 13*b* illustrates a bottom-up view of a variation of the trigger.

FIGS. 14*a* and 14*e* illustrate variations of a particle cassette.

FIG. 14*f* is a cross-sectional view of a variation of the particle cassette taken along cross-section W-W of FIG. 14*b*.

FIG. 14*g* is a cross-sectional view of another variation of the particle cassette taken along cross-section W-W of FIG. 14*b*.

FIG. 14*h* is a cross-sectional view of yet another variation of the particle cassette taken along cross-section W-W of FIG. 14*b*.

FIG. 15*a* illustrates a variation of a male cassette part of the particle cassette.

FIG. 15*b* is a cross-sectional view of a variation of the male cassette part taken along cross-section J-J of FIG. 15*a*.

FIG. 16*a* illustrates a variation of a female cassette part of the particle cassette.

FIG. 16*b* is a cross-sectional view of a variation of the female cassette part taken along cross-section K-K of FIG. 16*a*.

FIG. 17*a* illustrates a rupturing of a variation of a particle cassette.

FIG. 17*b* illustrates a rupturing of another variation of the particle cassette.

FIG. 18 illustrates a rupturing of another variation of the particle cassette.

FIG. 19*a* illustrates a rupturing of another variation of the particle cassette.

FIG. 19*b* illustrates a rupturing of another variation of the particle cassette.

FIG. 20 illustrates a rupturing of a variation of the delivery device having two particle cassettes.

DETAILED DESCRIPTION

Detailed descriptions of embodiments of the invention are provided herein. It is to be understood, however, that the present invention may be embodied in various forms. Therefore, the specific details disclosed herein are not to be interpreted as limiting, but rather as a representative basis for teaching one skilled in the art how to employ the present invention in virtually any detailed system, structure, or manner.

Various embodiments of the invention will now be described. The following description provides specific details for a thorough understanding and enabling description of these embodiments. One skilled in the art will understand, however, that the embodiments may be practiced without many of these details. Additionally, some well-known structures or functions may not be shown or described in detail so as to avoid unnecessarily obscuring the relevant description of the various embodiments.

The terminology used in the description presented below is intended to be interpreted in its broadest reasonable manner, even though it is being used in conjunction with a detailed description of certain specific embodiments of the invention. Certain terms may even be emphasized below. Any terminology intended to be interpreted in any restricted manner, however, will be overtly and specifically defined as such in this detailed description section.

Figure 1A:
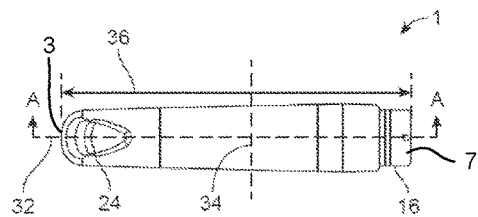
FIG. 1*a* illustrates a variation of a delivery device.

FIG. 1a illustrates a variation of a delivery device 1. The delivery device 1 can deliver particles 216 (see FIGS. 14f and 17) to a treatment surface 11 (see FIG. 1k). The treatment surface 11 can be an organ surface such as the skin or dermis. The particles 216 can include therapeutics, pharmaceuticals, genetic material, biologics, or a combination thereof in solid or particulate form. In one variation, the delivery device 1 can be a needleless syringe. The delivery device 1 can have a device longitudinal axis 32, a device lateral axis 34, and a device length 36. The device length 36 can be between about 1400 mm and 1700 mm or more narrowly, between about 1600 mm and 1675 mm. The device length 36 can also be about 1450 mm, 1500 mm, 1550 mm, 1600 mm, 1650 mm, 1675 mm, and 1700 mm.

The delivery device 1 can have a case 22 (see FIG. 1b) having a handle end 3 and an injection end 7 distal to or opposite the handle end 3 along the device longitudinal axis 32. In one variation, the case 22 can be a substantially cylindrical case. In another variation, the case 22 can be a frustoconical case, a conical case, a cuboid case, a pyramidal case, a prismatic case, or a combination thereof.

The delivery device 1 can have a trigger 24 located on or protruding from a circumferential or side surface of the case 22 of the delivery device 1. The trigger 24 can be accessed through an opening on the circumferential surface or side surface of the handle end 3 of the case 22. In one variation, a user contact surface 25 (see FIG. 1c) of the trigger 24 can be substantially flush with the circumferential surface or side surface of the case 22. In another variation, the trigger 24 can be sunk into the case 22 and the user contact surface 25 of the trigger 24 can be radially inward from the circumferential surface of the case 22. In yet another variation, the trigger 24 can protrude from or extend beyond the case 22 and the user contact surface 25 of the trigger 24 can be radially outward from the circumferential surface or the side surface of the case 22. The trigger 24 can be located or positioned at the handle end 3 of the case 22. The trigger 24 can be located or positioned proximal to the handle end 3 of the case 22. The trigger 24 can be located superior to the halfway point of the device longitudinal axis 32 when the injection end 7 of the delivery device 1 is facing down.

The delivery device 1 can have a silencer 5 at the injection end 7 of the delivery device 1. The silencer 5 can reduce the sound produced by the delivery device 1 when the delivery device 1 is actuated. The silencer 5 can have a radial diameter smaller than the radial diameter of the portion of the case 22 in contact with the silencer 5.

Figure 1B:
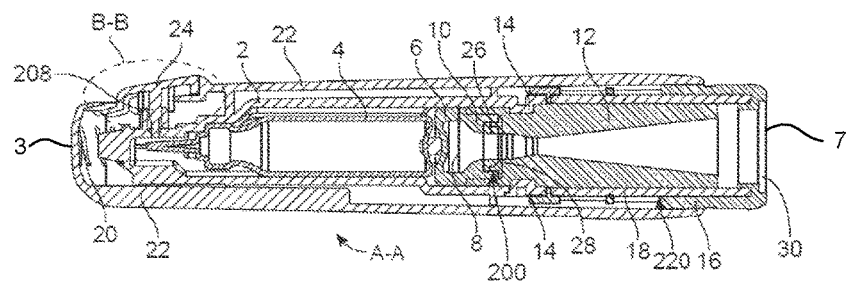

FIG. 1b is a cross-sectional view of a variation of the delivery device 1 of FIG. 1a taken along cross-section A-A. FIG. 1b illustrates that the delivery device 1 can have an inner housing 2, a gas supply 4, a compliant ball spacer (CBS) 6, one or more filters 8, an expansion chamber 10, a nozzle 12, a retainer 14, the silencer 5 having a silencer cover 16 and a silencer packing material 18, a spring 20, the case 22, the trigger 24, a particle cassette 200 having a male cassette part 26 and a female cassette part 28, a delivery port 30, or any combination thereof.

In one variation, the inner housing 2 can be a substantially cylindrical housing. In another variation, the inner housing 2 can be a cuboid housing, a conical housing, a frustoconical housing, a pyramidal housing, a prismatic housing, or a combination thereof. The gas supply 4 can be a pressurized gas container, a one-shot gas container, a pressurized cartridge, or a combination thereof.

The silencer 5 can include a silencer cover 16 and the silencer packing material 18. The silencer cover 16 can be toroidal, cylindrical, conical, frustoconical, or a combination thereof.

Figure 1C:
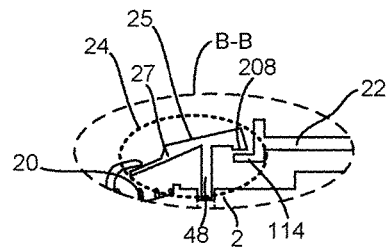
FIG. 1*c* is a close-up view B-B of a variation of a trigger.

FIG. 1c is a close up view B-B of a variation of the trigger 24 of the delivery device 1. The trigger 24 can have a trigger top 27 and a trigger pin 48. The trigger top 27 can have the user contact surface 25 at the top or radially outward surface of the trigger top 27. The trigger top 27 can have a trigger seat 208 on an underside or radially inward side of the trigger top 27. FIG. 1c illustrates that a safety interlock 114 of the delivery device 1 can impede the actuation of the trigger 24 when a user applies a radially inward force to the user contact surface 25 of the trigger top 27. The safety interlock 114 can impede the actuation of the trigger 24 by impeding the radially inward depression of the trigger 24. The safety interlock 114 can impede the actuation of the trigger 24 by blocking or abutting the trigger seat 208 of the trigger 24. The safety interlock 114 can impede the actuation of the trigger 24 by preventing the trigger pin 48 from being depressed radially inward.

The safety interlock 114 can be fixed to or extend from the case 22. For example, as illustrated in FIG. 1c, the safety interlock 114 can be a substantially flat or planar extension of the case 22. As illustrated in FIG. 1c, the trigger seat 24 can be substantially flat or planar. The substantially flat surface of the trigger seat 208 can rest or push against the safety interlock 114 to impede the depression or activation of the trigger 24. The safety interlock 114 can impede the actuation of the trigger 24 to prevent the unintentional release of a pressurized gas 100 (see FIGS. 7c-7e for an example illustration of the pressurized gas 100).

Figure 1D:
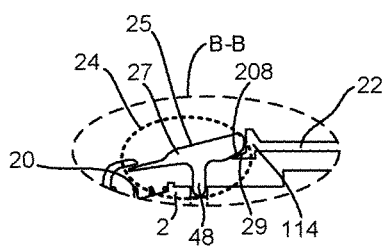
FIG. 1*d* is a close-up view B-B of another variation of the trigger.

FIG. 1d is a close up view B-B of a variation of the trigger 24 of the delivery device 1. FIG. 1d illustrates that the safety interlock 114 can have a triangular impeding element 29 extending from a tip of the safety interlock 114. The triangular impeding element 29 can have a sloped surface configured to contact or abut a congruently sloped surface of the trigger seat 208 to impede the actuation of the trigger 24.

Figure 1E:
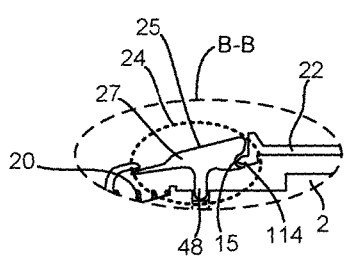
FIG. 1*e* is a close-up view B-B of another variation of the trigger.

FIG. 1e is a close up view B-B of another variation of the trigger 24 of the delivery device 1. FIG. 1e illustrates that the safety interlock 114 can be inserted into a notch 15 of the trigger top 27. The notch 15 can be a groove, divot, or opening in the trigger top 27. The notch 15 can be located above the trigger seat 208. The notch 15 can surround or encompass a portion of the safety interlock 114, such as the tip of the safety interlock 114. When the safety interlock 114 is inserted into the trigger top 27, the trigger 24 can be impeded from being depressed radially inward into the case 22 of the delivery device 1.

Figure 1F:
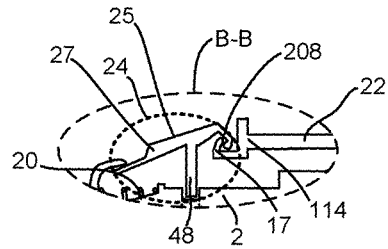
FIG. 1*f* is a close up view B-B of yet another variation of the trigger.

FIG. 1f is a close up view B-B of another variation of the trigger 24 of the delivery device 1. Figure if illustrates that the safety interlock 114 can have a latch 17 disposed at the tip of the safety interlock 114. As illustrated in FIG. 14, trigger seat 208 can be configured as a receptor or counterpart for the latch 17. The latch 17 can engage with the trigger seat 208 or receptor to impede the depression or actuation of the trigger 24.

In these and other variations, the delivery device 1 can have a tab or safety cover extending over or covering a portion of the safety interlock 114 and the trigger 24. The tab or safety cover can be bent out of the way of the trigger 24 or be broken or torn off before the safety interlock 114 can be disengaged from the trigger 24. For example, the tab or safety cover can be degraded by heat, such as the heat from a user's finger after five seconds, before permitting the safety interlock 114 to be disengaged from the trigger 24.

Figure 1G:
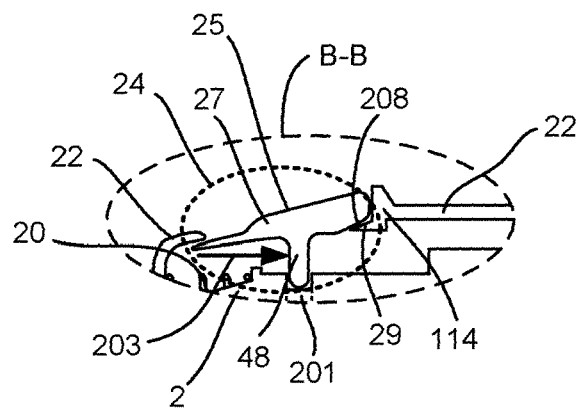
FIG. 1*g* is a close up view B-B of a variation of a safety interlock in a locked position.

FIG. 1g illustrates that the spring 20 can exert or apply a spring force 203 parallel to or along the device longitudinal axis 32 (see FIG. 1a) on the inner housing 2 of the delivery device 1 toward the injection end 7 of the delivery device 1. As illustrated in FIG. 1g, the trigger pin 48 can be disposed in or encompassed by an access channel 201 of the inner housing 2. The access channel 201 can be a bore or opening in the inner housing 2.

The spring force 203 applied to the inner housing 2 can transmit an equivalent longitudinal force to the trigger pin 48. This transmitted force can maintain the locked position of the trigger 24 by ensuring the trigger 24 is forced against the safety interlock 114 and the trigger seat 208 is in continuous contact with the safety interlock 114. The trigger 24 will remain in such a locked position as long as there is no countervailing force large enough to overcome the spring force 203 exerted by the spring 20 against the inner housing 2.

Figure 1H:
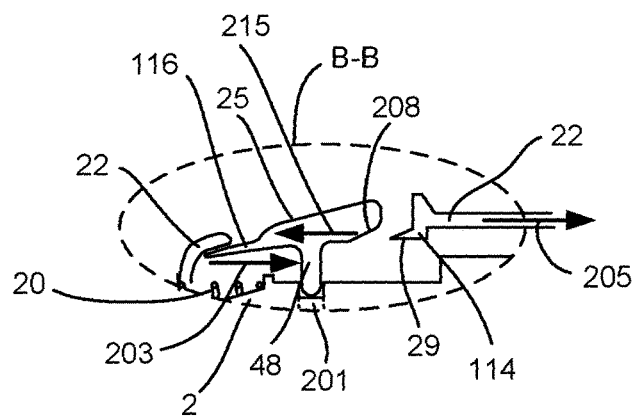
FIG. 1*h* is a close up view B-B of a variation of the safety interlock being disengaged.

FIG. 1h illustrates that the trigger 24 can overcome the spring force 203 and be slidably translated toward the handle end 3 of the delivery device 1, as shown by arrow 215. The trigger 24 can be slidably translated parallel with the device longitudinal axis 32. The trigger 24 and the case 22 can be translated with respect to each other. For example, a user can apply a force in the direction of arrow 215 to the user contact surface 25 of the trigger top 27 to translate the trigger 24 toward the handle end 3. In this example, a stepped-down portion 116 of the trigger 24 can slide against a portion of the case 22 at the handle end 3 of the delivery device 1. The stepped-down portion 116 of the trigger can slide against a radially inward surface of the portion of the case 22 at the handle end 3 of the delivery device 1.

The stepped-down portion 116 of the trigger 24 can be a portion of the trigger top 27 located toward the handle end 3 of the delivery device 1 and having a surface that is set radially inward from the user contact surface 25 of the trigger 24. The stepped-down portion 116 of the trigger 24 can be sloped or angled relative to the device longitudinal axis 32. When the stepped-down portion 116 of the trigger 24 slides against the radially inward surface of the case 22, the radially inward surface of the case 22 can apply a radially inward force on the trigger top 27 to elevate, tilt, or translate the trigger seat 208 away or radially outward from the safety interlock 114. By elevating, tilting, or translating the trigger seat 208 away or radially outward from the safety interlock 114, the case 22 can disengage the trigger 24 from the safety interlock 114. In this variation, the trigger top 27 can serve as a lever and the trigger pin 48 can serve as the fulcrum of the lever.

In another variation, the case 22, including the safety interlock 114, can be slidably translated toward the injection end 7 of the delivery device 1. The case 22 and the safety interlock 114 can be translated in the direction of arrow 205. In this example, the case 22, including the safety interlock 114 affixed to or serving as a part of the case 22, can disengage from the trigger 24, including the trigger seat 208, and no longer impede or interfere with the radially inward depression or actuation of the trigger 24.

Figure 1I:
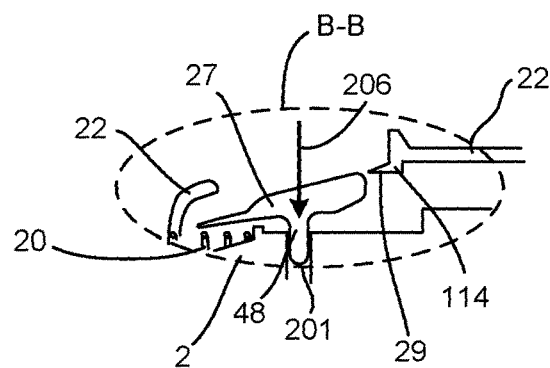
FIG. 1*i* is a close up view B-B of a variation of the safety interlock disengaged.

FIG. 1i illustrates that after the safety interlock 114 is disengaged from the trigger 24, the trigger 24 can be depressed or translated radially inward in the direction of arrow 206 toward a midline of the delivery device 1 unimpeded by the safety interlock 114.

Figure 1J:
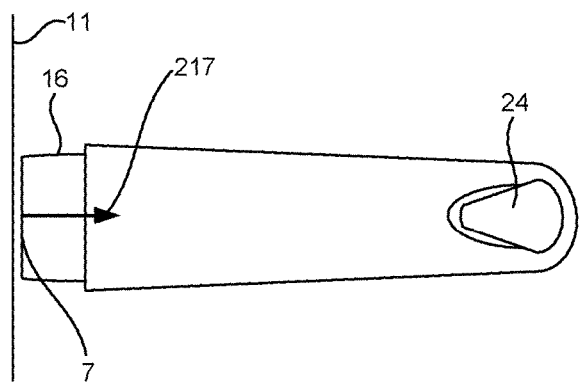
FIG. 1*j* illustrates a variation of the delivery device being applied to a treatment surface.

FIG. 1j illustrates that when the injection end 7 of the delivery device 1 is pressed against or makes contact with the treatment surface 11, such as dermis or skin surface of a patient, the inner housing 2 of the delivery device 1 can be translated in the direction of arrow 217 toward the handle end 3 of the delivery device 1. The inner housing 2 of the delivery device 1 can be translated in the direction of arrow 217 when the silencer cover 16, the delivery port 30, or a combination thereof is pressed against or makes contact with the treatment surface 11. The inner housing 2 can be translated within the case 22.

Figure 1K:
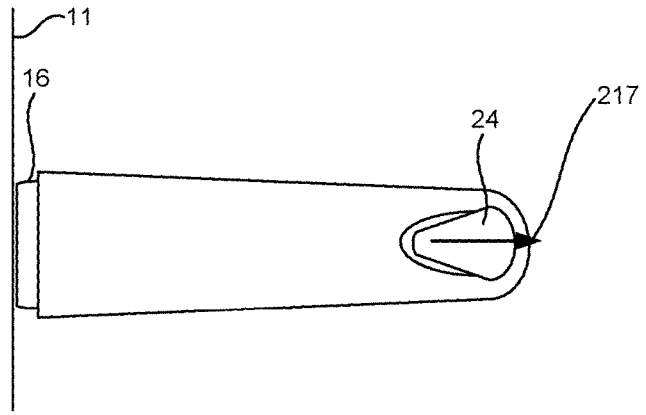
FIG. 1*k* illustrates a variation of the delivery device applied to the treatment surface.

FIG. 1k illustrates that the movement or translation of the silencer cover 16 can also translate or move the inner housing 2, the trigger pin 48, or a combination thereof toward the handle end 3 of the delivery device 1. When the inner housing 2 is translated in the direction of arrow 217, the safety interlock 114 can be disengaged from the trigger 24 as discussed above and/or illustrated in FIGS. 1g-1h.

Figure 1L:
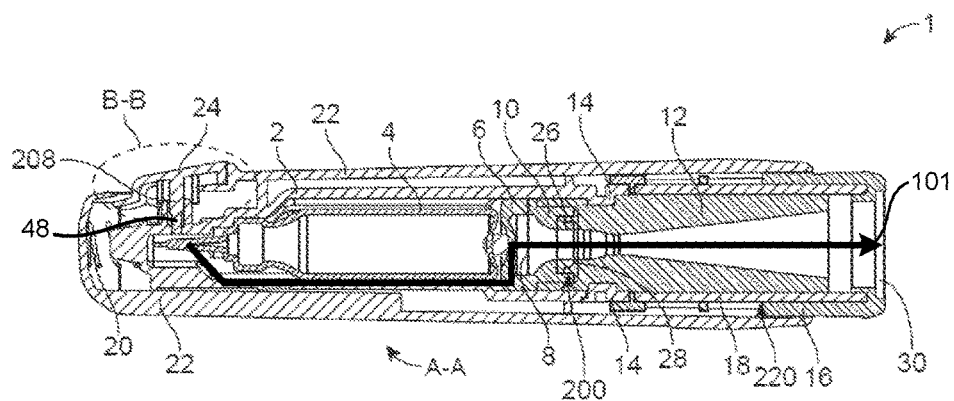
FIG. 1*l* illustrates a variation of a gas flow passageway through the delivery device.

FIG. 1l illustrates that when the trigger 24 is pressed or actuated after the safety interlock 114 is disengaged, the trigger pin 48 can puncture or breach the gas supply 4 to release the pressurized gas 100 from the gas supply 4. In another variation, the trigger pin 48 can displace or translate a secondary pin, such as a secondary pin within the inner housing 2, to puncture or breach the gas supply 4. In yet another variation, a tip of the trigger pin 48 distal to the trigger top 27 can serve as a cap or plug for the gas supply 4 and actuating the trigger 24 can involve displacing the cap or plug from the gas supply 4, thereby releasing the pressured gas from the gas supply 4.

When the trigger 24 is pressed or actuated, the trigger 24 can remain in the pressed or actuated position or state to inform a user that the delivery device 1 has been used or compromised. Alternatively, the trigger 24 can return to its original or unactuated state after actuation. In another variation, the trigger 24 can return to its original or unactuated state when a new instance of the gas supply 4 or new particle cassette 200 are replaced in the delivery device 1.

FIG. 1l illustrates that when the gas supply 4 is breached, the pressurized gas 100 can escape or flow from the gas supply 4 through a gas flow passageway 101. The pressurized gas 100 from the gas supply 4 can flow from the handle end 3 of the delivery device 1 to the delivery port 30 at the injection end 7 of the delivery device 1. The gas flow passageway 101 can include openings, channels, chambers, or portions of the gas supply 4, the inner housing 2, the CBS 6, the filters 8, the expansion chamber 10, the particle cassette 200, the nozzle 12, the silencer 5, the case 22, or a combination thereof. Some portions of the gas flow passageway 101 can be pre-defined or preset by walls or surfaces of the gas supply 4, the inner housing 2, the CBS 6, the filters 8, the expansion chamber 10, the particle cassette 200, the nozzle 12, the silencer 5, the case 22, or a combination thereof. Other portions of the gas flow passageway 101 can be created or shaped by the pressurized gas 100 as the pressurized gas 100, the particles 216 carried by the pressurized gas 100, or a combination thereof as the pressurized gas 100 flows downstream from the handle end 3 of the delivery device 1 to the injection end 7 or from the gas supply 4 to the delivery port 30.

The particle cassette 200 can house or contain the particles 216. The pressurized gas 100 can carry or deliver the particles 216 housed in the particle cassette 200 through the nozzle 12. The pressurized gas 100 can enter the particle cassette 200 by breaking through or breaching a cassette membrane 210 (see FIG. 14a) at an upstream end of the particle cassette 200. In one variation, the pressurized gas 100 can also break through another cassette membrane 210 at a downstream end of the particle cassette 200. In this variation, the pressurized gas 100 can create a part of the gas flow passageway 101 and carry the particles 216 housed in the particle cassette 200 downstream into the portion of the nozzle 12 serving as part of the gas flow passageway 101. The pressurized gas 100 can carry the particles 216 by translating or imbuing the particles 216 with energy from the pressurized gas 100.

In another variation, the pressurized gas 100 can translate or imbue the particles 216 in the particle cassette 200 with enough energy to break through the other cassette membrane 210 at the downstream end of the particle cassette 200. The nozzle 12 can accelerate the velocity of the pressurized gas 100, the particles 216, or a combination thereof. The pressurized gas 100, the particles 216, or a combination thereof can exit the delivery device 1 through the delivery port 30. The delivery device 1 can deliver the particles 216 to the treatment surface 11 in a uniform manner.

Figure 2A:
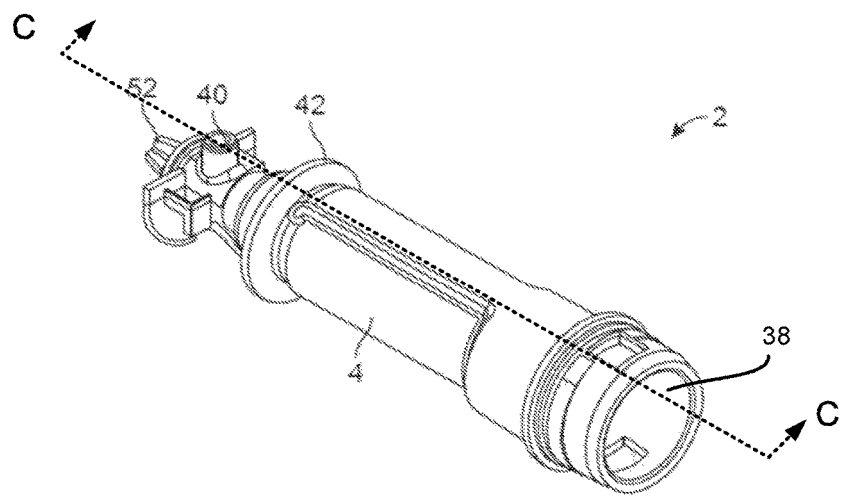
FIG. 2*a* illustrates a variation of the inner housing.

FIG. 2a is perspective view of a variation of the inner housing 2 of the delivery device 1. The inner housing 2 can be composed or made of a metal, a polymer, or a composite thereof. For example, the inner housing 2 can be made of polycarbonate. The inner housing 2 can have a housing opening 38, a housing port 40, a housing tip 52, a housing bracket 42, or a combination thereof. The housing opening 38 can be on an end of the inner housing 2 distal from the housing tip 52. For example, when the inner housing 2 is situated in the case 22, the housing opening 38 can be at the injection end 7 of the delivery device 1 and the housing tip 52 can be at the handle end 3.

The housing opening 38 can allow the gas supply 4 to be inserted into the inner housing 2. The housing port 40 can be located proximal to the housing tip 52 and distal from the housing opening 38. In one variation, the housing port 40 can be a substantially cylindrical port. In another variation, the housing port 40 can be a substantially cuboidal port.

Figure 2B:
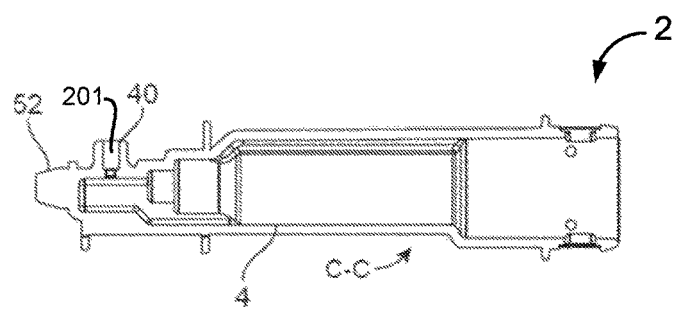
Figure 2C:
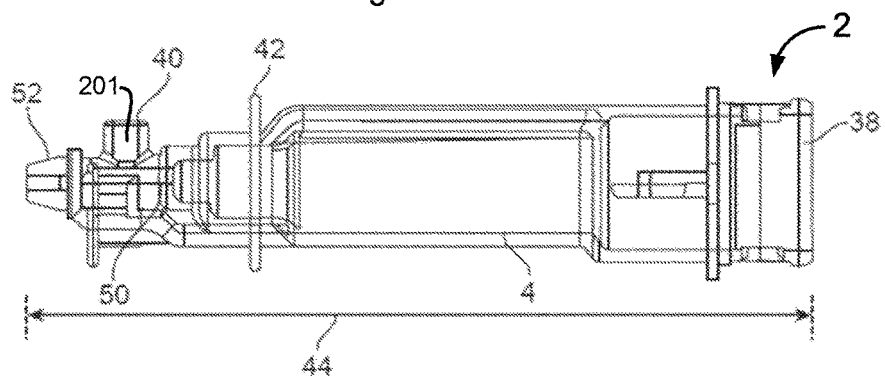
FIG. 2*c* is a side transparent view of a variation of the inner housing.

FIG. 2b is a cross-sectional view of an example variation of the inner housing 2 of FIG. 2a taken along cross-section C-C. FIG. 2b illustrates that the housing port 40 can be located on a lateral or circumferential side of the inner housing 2. The housing port 40 can be perpendicular to a longitudinal axis of the inner housing 2. The housing port 40 can extend radially outward from the inner housing 2. The housing port 40 can house or surround the trigger pin 48 of the trigger 24.

For example, a portion of the trigger pin 48 can be disposed or located in the access channel 201 of the housing port 40. The access channel 201 can be the space surrounded by the walls of the housing port 40.

FIG. 2b also illustrates that the inner housing 2 can house or hold the gas supply 4. The gas supply 4 can be filled with the pressurized gas 100 such as helium, oxygen, carbon dioxide, or a combination thereof. The pressurized gas 100 can exit the housing opening 38 when the trigger 24 (see FIGS. 1c-1i) is actuated. The trigger 24 can be actuated when the trigger pin 48 enters the access channel 201. The delivery device 1 can be actuated by the trigger 24 when the trigger pin 48 punctures, breaks, or displaces a component or piece of the gas supply 4 such as the spout 50.

In one variation, the trigger pin 48 can be coupled or physically connected to the spout 50. In another variation, the trigger pin 48 can displace, move, or translate a secondary pin that can be used to breach or puncture the gas supply 4. For example, the trigger pin 48 can displace, move, or translate a secondary pin that can break or puncture the spout 50.

FIG. 2*c* illustrates that the inner housing 2 can have a housing length 44. The housing length 44 can be between about 90 mm and 120 mm, more narrowly, between about 100 mm and 115 mm. The housing length 44 can be about 105 mm, about 108 mm, about 108.5 mm, about 110 mm, or about 115 mm.

As illustrated in FIG. 2*c*, the housing bracket 42 can stabilize the inner housing 2 within the case 22. The housing bracket 42 can be a circular or toroidal latch. The housing bracket 42 can extend radially outward from the center of the inner housing 2. The housing bracket 42 can be perpendicular to the longitudinal axis of the inner housing 2. The housing bracket 42 can be coupled and/or secured to the retainer 14. The housing bracket 42 can fit within the retainer 14. The housing bracket 42 can move the inner housing 2 proximally relative to the case 22 when the device 1 is pressed against the surface. The housing tip 52 can be on the proximal end of the inner housing 2. The housing tip 52 can apply force against the spring 20 when the distal end of the delivery device 1 is pressed against the surface. The spring 20 can be secured, attached, and/or coupled to the housing tip 52 and/or the case 22.

The inner housing 2 can have an electronic sensor, a mechanical sensor, or a combination thereof. The electronic sensor, the mechanical sensor can alert the user to ensure that the gas supply 4 is securely housed by or located in the inner housing 2. Another sensor or the same sensor can also determine an amount of the pressurized gas 100 currently held by the gas supply 4. For example, the sensor can inform a user of the delivery device 1 that the gas supply 4 is full or empty. The inner housing 2 can have an ejection mechanism to eject the gas supply 4 from the inner housing 2. The ejection mechanism can be coupled to the inner housing 2, the case 22, or a combination thereof.

FIG. 3*a* is a perspective view of an example variation of the gas supply 4. As illustrated in FIG. 3*a*, the gas supply 4 can be a substantially cylindrical container having the spout 50 at one end. When the gas supply 4 is secured or housed by the inner housing 2, a portion of the spout 50 can be located radially inward from the housing port 40 of the inner housing 2. The spout 50 can be located proximal to the handle end 3 of the delivery device 1.

FIG. 3*b* is a cross-sectional view of an example variation of the gas supply 4 of FIG. 3*a* along cross-section D-D. FIG. 3*b* illustrates that the gas supply 4 can have a supply length 54, a supply compartment 56, a supply bevel 58, or a combination thereof. The supply compartment 56 can be configured to house a gas under pressure. The gas can be helium, oxygen, carbon dioxide, or a combination thereof. The gas supply 4 can be constructed or composed of a metal such as aluminum or steel, a polymer such as polycarbonate, or a composite thereof.

The supply length 54 can be between about 65 mm and 75 mm and, more narrowly, between about 69 mm and 73 mm. The supply length 54 can also be about 70 mm, about 70.8 mm, about 71 mm, about 71.3 mm, or about 72 mm.

The supply compartment 56 can have an inner wall and an outer wall. The pressurized gas 100 in the supply compartment 56 can be charged to a pressure greater than about 10 bar. The pressurized gas 100 can in the supply compartment 56 also be charged to a pressure from about 10 bar to about 60 bar.

The supply bevel 58 can be located at an end of the gas supply 4 distal to the spout 50. The supply bevel 58 can be formed as a divot or concavity intruding into the supply compartment 56. The supply bevel 58 can be coupled to the CBS 6. The supply bevel 58 can have a screen to prevent pressurized gas 100 from leaking. The supply bevel 58, the screen, or a combination thereof can provide and strength for the gas supply 4 to prevent the gas supply 4 from bursting.

Figure 3A:
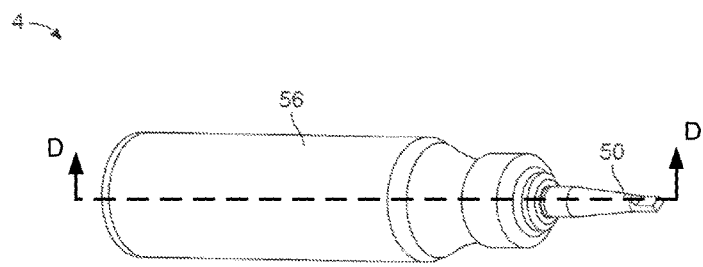
FIG. 3*a* is a variation of a gas supply.
Figure 3B:
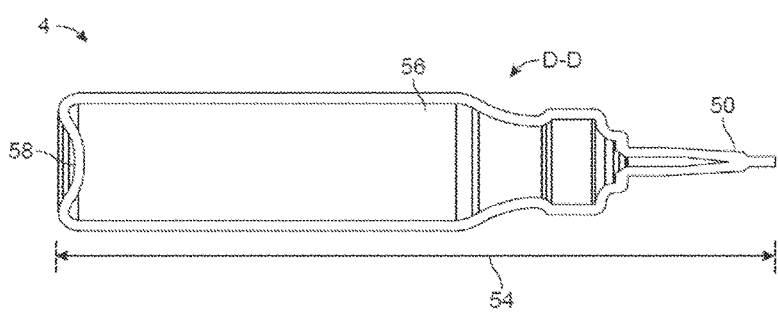

When the delivery device 1 is actuated, such as by a radially inward depression of the trigger 24, the pressurized gas 100 can flow at a high velocity from the supply compartment 56 to the treatment surface 11. The pressurized gas 100 can also carry the particles 216 from the particle cassette 200 to the treatment surface 11 at high velocity. As illustrated in FIGS. 3a and 3b, the spout 50 be a substantially conical or tapered end of the gas supply 4 distal from the supply bevel 58.

Figure 3C:
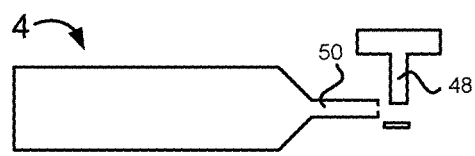
FIGS. 3*c* through 3*e* illustrate variations of a trigger interacting with the gas supply.

FIG. 3c illustrates that the trigger pin 48 can snap off or displace a portion of the spout 50 from the remainder of the gas supply 4. By snapping off or displacing the portion of the spout 50 from the remainder of the gas supply 4, the trigger pin 48 can separate the displaced or broken off portion of the spout 50 from the remainder of the gas supply 4. The trigger pin 48 can snap off or displace a portion of the spout 50 when the safety interlock 114 is disengaged from the trigger 24 and the trigger pin 48 is translated further into the access channel 201.

Figure 3D:
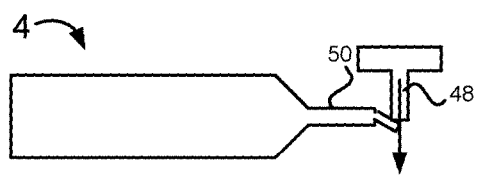

FIG. 3d illustrates that instead of snapping off or separating a portion of the spout 50 from the remainder of the gas supply 4, the trigger pin 48 can apply a displacing force to a tip or head of the spout 50. The pressurized gas 100 can flow or escape from an opening in the spout 50 when the tip or head of the spout 50 is displaced relative to its original position. Also, in this variation, the spout 50, the gas supply 4, or a combination thereof can once again be sealed or closed when the trigger pin 48 is translated radially outward and is no longer displacing or impinging on the tip or head of the spout 50. In this variation, the tip or head of the spout 50 is never severed or completely separated from the remainder of the spout 50 or gas supply 4.

Figure 3E:
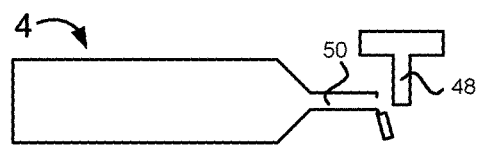

FIG. 3e illustrates that a tip or head of the spout 50 can be attached or connected to the remainder of the spout 50 when the trigger pin 48 displaces or partially separates the tip or head of the spout 50 from the remainder of the spout 50. In this variation, the pressurized gas 100 is prevented from carrying the displaced tip or head of the spout 50 toward the injection end 7 of the delivery device 1 and the treatment surface 11. By ensuring the tip or head of the spout 50 remains attached or connected to the rest of the spout 50, the delivery device 1 can prevent the tip or head of the gas supply 4 from being injected into an organ of the patient such as the skin of the patient.

Figure 3F:
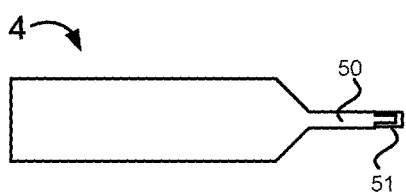
FIG. 3*f* illustrates another variation of the gas supply.

FIG. 3f illustrates that the spout 50 can be encompassed or covered by a screen 51. The screen 51 can prevent the pressurized gas 100 from leaving from the gas supply 4 before the delivery device 1 is actuated. The trigger pin 48 can pierce the screen 51 when a user presses the trigger 24. In another variation not shown in FIG. 3f, the screen 51 can encompass or cover the entire gas supply 4.

Figure 4A:
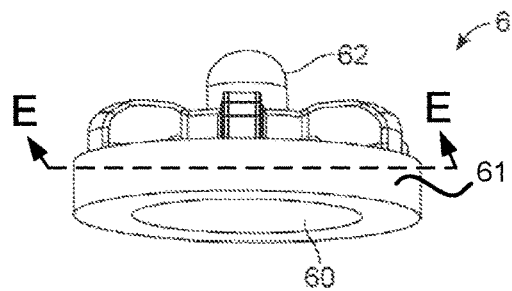
FIG. 4*a* illustrates a variation of a compliant ball spacer.

FIG. 4a is a perspective view of a variation of the CBS 6 of the delivery device 1. As illustrated in FIG. 4a, the CBS 6 can have one or more CBS openings 60, a CBS base 61, and a CBS tip 62. The CBS 6 can be composed or made of a polymer such as a high impact polystyrene (HIPS), a high performance elastomer such as Santoprene™, or a combination thereof. For example, the CBS tip 62 can be made of Santoprene™ and the CBS base 61 can be made of HIPS. As illustrated in FIG. 4a, the CBS 6 can be formed as a gasket. For example, the CBS 6 can be formed as a substantially circular gasket. In other variations, the CBS 6 can be formed as a triangular or square gasket.

Figure 4B:
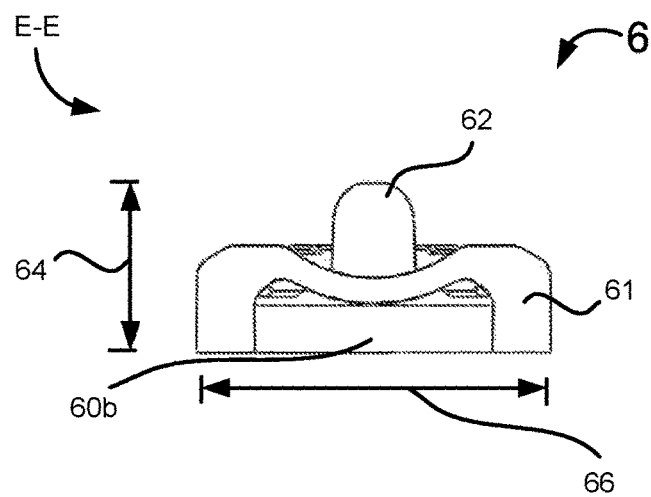

FIG. 4b is a cross-sectional view of an example variation of the CBS 6 of FIG. 4a taken along cross-section E-E. FIG. 4b illustrates that the CBS 6 has a CBS length 64, a CBS diameter 66, a number of radial CBS openings 60a (see FIG. 4c), a base CBS opening 60b at the CBS base 61, or a combination thereof.

The CBS diameter 66 can be between about 15 mm and 20 mm. The CBS diameter 66 can also be between about 18 mm and 19 mm. For example, the CBS diameter 66 can be about 18 mm, about 18.8 mm, or about 19 mm. The CBS length 64 can be between about 8 mm and 10 mm. The CBS length 64 can also be about 8.8 mm, about 9 mm, or about 9.2 mm.

The CBS 6 can be coupled to the gas supply 4, the filter 8, the nozzle 12, the particle cassette 200 such as the male cassette part 26, the female cassette part 28, or a combination thereof, the expansion chamber 10, or any combination thereof. For example, the CBS tip 62 can be coupled to or face the gas supply 4. The CBS base 61 can be coupled to the filter 8. The CBS 6 can prevent or reduce the leakage of gas from the gas supply 4. The CBS 6 can prevent gas from passing through the CBS 6 to the filters 8, the expansion chamber 10, or a combination thereof until enough pressure has built up.

The CBS 6 can have a number of radial CBS openings surrounding the CBS tip 62 and a base CBS opening 60b at the CBS base 61. As illustrated in FIG. 4b, a channel can form between the radial CBS openings 60a and the base CBS opening 60b.

Figure 4C:
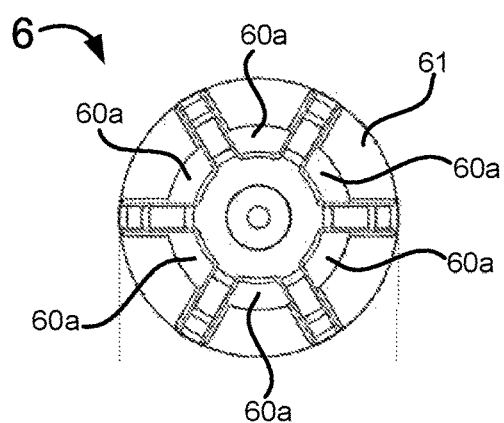
FIG. 4*c* is a top plan view of a variation of the compliant ball spacer.

FIG. 4c is a top plan view of an example variation of the CBS 6. The radial CBS openings 60a can surround the CBS tip 62.

Figure 5A:
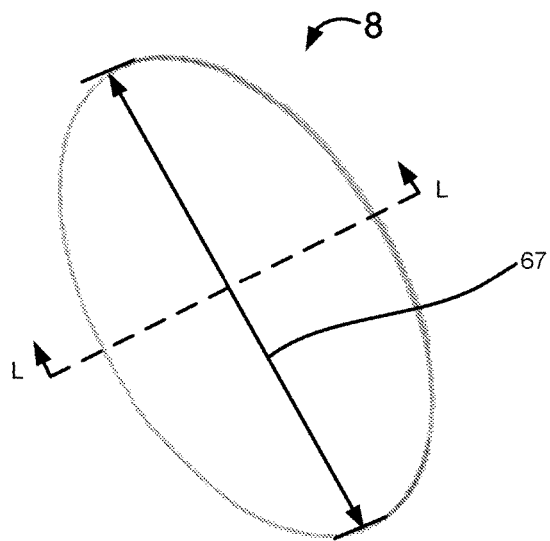
FIG. 5*a* illustrates a variation of a filter.

FIG. 5a illustrates that the filters 8 can filter extraneous matter, such as dust, metal or polymer particles, or broken off pieces of the spout 50 present in any chambers or channels of the delivery device 1 or carried by the pressurized gas 100 released from the gas supply 4. In one variation, the delivery device 1 can have one, two, or three filters 8 disposed in between the CBS 6 and the expansion chamber 10. The filters 8 can be made or manufactured from a metal, a polymer, or a composite thereof. For example, the filters 8 can be made of stainless steel, such as 316L stainless steel. Also, for example, the filters 8 can be made of polypropylene, or a composite of polypropylene and 316L stainless steel. The filter 8 can be circular, oval, triangular, rectangular, square, or any combination thereof. The filter 8 can be porous, mesh, or any other material that can allow the pressurized gas 100 to flow through the filter 8 but can impeded or hinder the flow of extraneous matter carried or delivered by the pressurized gas 100. The filter 8 can have at least one, two, three, four, or more filter ports, perforations, or holes. The ports, perforations, or holes can be triangular, square, diamond, rectangular, oval, circular, or any combination thereof.

The filter 8 can be positioned or affixed inside a channel or chamber, at an opening of a channel or chamber, or a combination thereof. For example, the filter 8 can be positioned or affixed at the radial CBS openings 60a, the base CBS opening 60b, or a combination thereof. The filter 8 can be positioned or affixed inside the expansion chamber 10, the nozzle 12, the gas supply 4, or a combination thereof. The filter 8 can be positioned or affixed at the first cassette port 213a, the second cassette port 213b, or any combination thereof.

The filter 8 can have a filter diameter 67. The filter diameter 67 can be between about 17 mm and 20 mm, or more narrowly, between about 18 mm and 19 mm. The filter diameter 67 can be about 18 mm, about 18.5 mm, or about 19 mm.

Figure 5B:
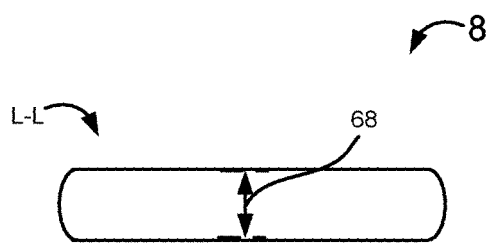

FIG. 5b is a cross-sectional view of an example variation of the filter 8 of FIG. 5a taken along cross-section L-L. FIG. 5b illustrates that the filter 8 can have a filter thickness 68. The filter thickness 68 can be between about 0.1 mm and about 0.25 mm, more narrowly, between about 0.1 mm and 0.2 mm, for example, about 0.1 mm, about 0.15 mm, and about 0.2 mm. The filter 8 can be double-paned.

Figure 5C:
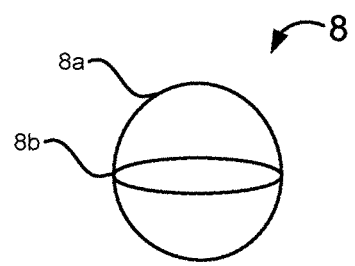
FIG. 5*c* is another variation of the filter.

FIG. 5c illustrates that the filter 8 can comprise multiple filters 8 arranged in different geometric configurations or arrangements. For example, FIG. 5c illustrates that the filter 8 can comprise a spherical filter 8a and a circular filter 8b inside the spherical filter 8a. In one variation, the spherical filter 8a can comprise larger perforations or holes than the circular filter 8b affixed inside the spherical filter 8a. In this variation, the spherical filter 8a can act as a coarse filter for filtering out larger particulates or extraneous matter and the circular filter 8b can act as a fine filter for filtering out small particulates or extraneous matter.

Figure 6A:
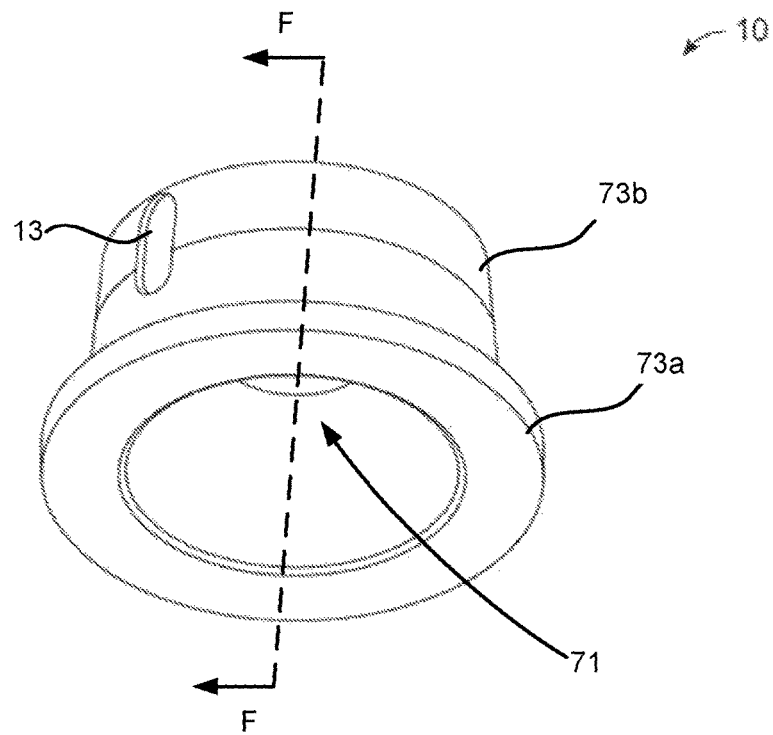
FIG. 6*a* illustrates a variation of an expansion chamber.

FIG. 6a is a perspective view of an example variation of the expansion chamber 10 of the delivery device 1. FIG. 6a illustrates that the expansion chamber 10 can be configured to hold or secure the particle cassette 200. The expansion chamber 100 can allow the pressurized gas 100 from the gas supply 4 to build up in the expansion chamber 100. For example, the expansion chamber 100 can allow the gas pressure of the pressurized gas 100 to build up to a pressure above a pre-determined threshold. The expansion chamber 100 can allow the gas pressure of the pressurized gas 100 to build up to 10 bar, between 10 bar and 60 bar, or between 10 bar and 100 bar.

The expansion chamber 10 can also accelerate the pressurized gas 100 toward the particle cassette 200. The expansion chamber 10 can have a chamber flange 73a and a chamber body 73b. The chamber flange 73a can be coupled to or contacting the CBS 6. The chamber body 73b can be coupled to or contacting the retainer 14. The chamber body 37b can house a portion of the particle cassette 200, such as the male cassette part 26.

The expansion chamber 100 can have a flow channel 71. The flow channel 71 can be a conduit or space defined by the first chamber opening 70a (see FIG. 6b) at one end of the flow channel 71 and the second chamber opening 70b (see FIG. 6b) at the other end of the flow channel 71. The flow channel 71 can be part of the gas flow passageway 101.

Figure 6B:
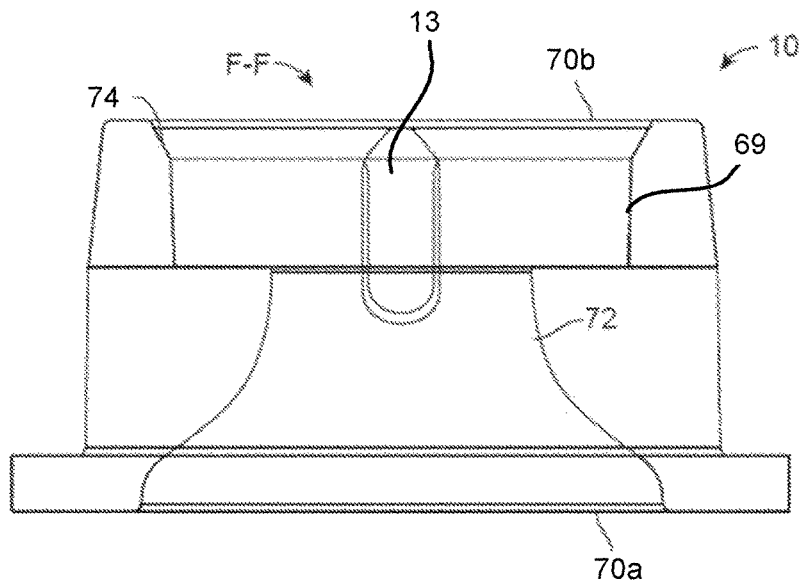

FIG. 6b is a cross-sectional view of an example variation of the expansion chamber 10 of FIG. 6a taken along cross-section F-F. FIG. 6b illustrates that the chamber body 73b can have a bell-shaped inner wall 72 and a cassette holding portion 69. The bell-shaped inner wall 72 can have a first diameter equivalent to the diameter of the first chamber opening 70a. The diameter of the bell-shaped inner wall 72 can taper and converge to a second diameter. The second diameter can be smaller than the first diameter.

The bell-shaped inner wall 72 can define the shape of the flow channel 71 at this part of the expansion chamber 10. The bell-shaped inner wall 72 can be configured to direct or congregate the pressurized gas 100 flowing from the gas supply 4 into a progressively smaller space. The bell-shaped inner wall 72 can ensure that the pressure of the pressurized gas 100 is built up as the pressurized gas 100 enters the expansion chamber 10 through the first chamber opening 70a.

The cassette holding portion 69 can house or secure a portion of the particle cassette 200. The cassette holding portion 69 can be configured in the shape of the particle cassette 200. For example, the cassette holding portion 69 can be shaped as a substantially cylindrical housing. The cassette holding portion 69 can have a diameter larger than the diameter of the bell-shaped inner wall 72 in contact or connected to the cassette holding portion 69.

The cassette holding portion 69 can have an outwardly expanding inner wall 74. The outwardly expanding inner wall 74 can define the shape of the second chamber opening 70b. The shape of the flow channel 71 can be defined by the bell-shaped inner wall 72, the cassette holding portion 68, the outwardly expanding inner wall 74, or a combination thereof.

The expansion chamber 10 can have at least one, two, or more expansion chamber ports 13. The expansion chamber port 13 can be shaped as an oval, a circle, a diamond, or any combination thereof. The expansion chamber port 13 can have one end that is arrow-shaped, another end that is circular shaped, or a combination thereof. The expansion chamber port 13 can be located on a side or circumferential surface of the expansion chamber 10. The expansion chamber port 13 can be located on the chamber body 73b. The expansion chamber port 13 can expose a portion of the flow channel 71 encompassed by the bell-shaped inner wall 72, the cassette holding portion 69, or a combination thereof.

The longitudinal axis of the expansion chamber port 13 can be parallel or perpendicular to the device longitudinal axis 32, the longitudinal axis of the expansion chamber 10, or a combination thereof. Although not shown in FIGS. 6a and 6b, it is contemplated that one or more additional expansion chamber ports 13 can be located along the circumferential or side surface of the expansion chamber 10. For example, a second expansion chamber port 13 can be located on a surface of the expansion chamber 10 diametrically opposed to the expansion chamber port 13 shown in FIGS. 6a and 6b. The expansion chamber ports 13 can allow some of the pressurized gas 100 to escape or vent out of the expansion chamber 10. The expansion chamber ports 13 can also allow the pressurized gas 100 to enter or circulate back into the expansion chamber 100.

Figure 7A:
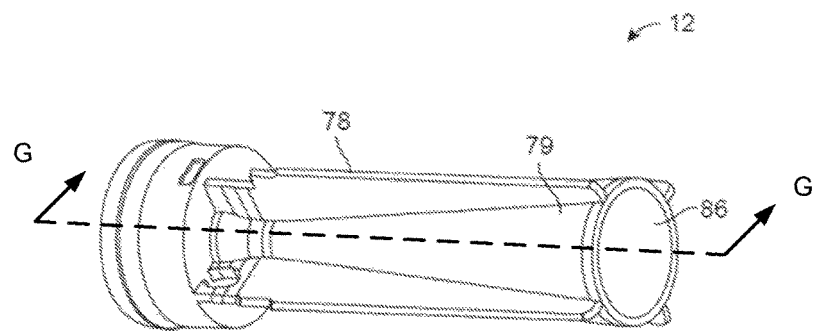
FIG. 7*a* illustrates a variation of a nozzle.

FIG. 7a is a perspective view of an example variation of the nozzle 12 of the delivery device 1. The nozzle 12 can be coupled or in contact with the expansion chamber 10, one or more filters 8, the particle cassette 200, or a combination thereof. The nozzle 12 can also be coupled or connected to the gas supply 4. The nozzle 12 can have an elongate portion 79 and one or more fins 78 coupled or protruding from an outer circumferential surface of the elongate portion 79. In the variation shown in FIG. 7a, the elongate portion 79 can be shaped as an extended cone having an elongate conical body. In the variation shown in FIG. 7c, the elongate portion 79 can be shaped as an elongate cylinder or tube having a uniform diameter throughout the elongate portion 79. The elongate portion 78 can open or flare out to a nozzle opening 86. When the elongate portion 79 is shaped as an extended cone, the diameter of the nozzle opening 86 can be greater than the diameter of all other cross-sections along the elongate portion 79.

The nozzle 12 can be constructed from a polymer, a metal, or a composite thereof. For example, the nozzle 12 can be constructed of polycarbonate. The nozzle 12 can contain or handle gas pressures between 10 bar and 100 bar, or more narrowly, between 10 bar and 60 bar. The nozzle 12 can accelerate the pressurized gas 100 through the elongate portion 79 at a pressure between 10 bar and 60 bar. The nozzle 12 can also accelerate pressurized gas 100 entering the nozzle 12 at between 10 bar and 60 bar.

The one or more fins 78 can be affixed to or protrude radially from the outer circumferential surface of the elongate portion 79. Two, three, or more fins 78 can be affixed to or protrude radially from the outer circumferential surface of the elongate portion 79. The radially outward side of the fins 78 can be coupled to the inner surface of the case 22, the inner housing 2, the silencer cover 16, or a combination thereof. The fins 78 can provide structural rigidity to the nozzle 12 when the nozzle 12 is housed or secured by the case 22, the inner housing 2, or a combination thereof. The fins 78 can also be coupled to a portion of the silencer 5, the silencer cover 16, the silencer packing material 18, or any combination thereof. The fins 8 can be affixed to protrude from the entire length of the elongate portion 79. The fins 78 can be configured so that the radial length or height of the fins 78 decrease as the radial diameter of the elongate portion 79 increases. For example, the radial length or height of the fins 78 can be greatest at an end of the elongate portion 79 distal from the nozzle opening 86.

Figure 7B:
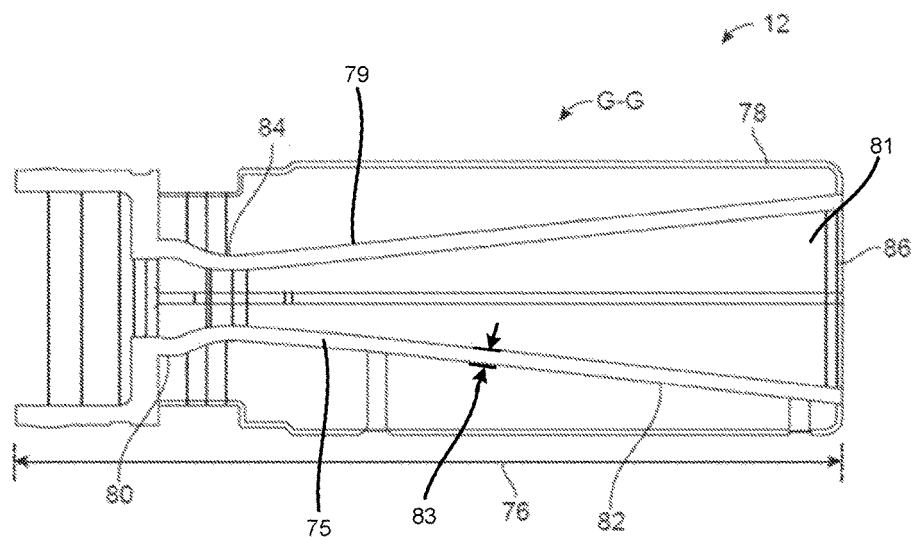

FIG. 7b is a cross-sectional view of an example variation of the nozzle 12 of FIG. 7a taken along cross-section G-G. FIG. 7b illustrates that the nozzle 12 can have a flow convergent section 80, a throat section 84, the elongate portion 79, or any combination thereof. When the elongate portion 79 is an extended cone, the elongate portion 79 can have a flow divergent section 82.

The nozzle 12 can have a nozzle wall 75 surrounding or encompassing a nozzle channel 81. The nozzle channel 81 can be the space defined by the flow convergent section 80, the throat section 84, the elongate portion 79, or any combination thereof.

The nozzle wall 75 can have a wall thickness 83. The wall thickness 83 can be between about 0.01 mm and 3.00 mm. The wall thickness 83 can also be between 0.50 mm and 2.00 mm. For example, the wall thickness 83 can be about 0.50 mm, 1.00 mm, 1.50 mm, or about 2.0 mm.

The nozzle 12 can also have a nozzle length 76. The nozzle length 76 can be between about 50 mm and 75 mm. The nozzle length 76 can also be between about 55 mm and 65 mm. For example, the nozzle length 76 can be about 65 mm.

The nozzle 12 can be coupled to the expansion chamber 10 at the flow convergent section 80. The nozzle channel 81 can begin at the flow convergent section 80, proceed through the throat section 84 and the flow divergent section 82 of the elongate portion 79, and end at the nozzle opening 86. The flow convergent section 80 and the flow divergent section 82 can be used to accelerate the pressurized gas 100 to supersonic speed or any other desired speed. For example, the pressurized gas 100 can first be brought to Mach 1 speed by proceeding through the flow convergent section 80 to the throat section 84. The pressurized gas 100 can then be further accelerated by the flow divergent section 82 to a steady state supersonic speed or any other desired speed. As illustrated in FIG. 7b, the radial diameter of the throat section 84 can be smaller than the radial diameter of any transverse cross-section of the elongate portion 79. In addition, the radial diameter of the throat section 84 can be smaller than the radial diameter of the flow convergent section 80. The radial diameter of the nozzle opening 86 can be larger than the radial diameter of the throat section 84 and the radial diameter of any transverse cross-section of the flow convergent section 80.

In one variation, the flow divergent section 82 of the elongate portion 79 can be used to accelerate the particles 216 and disperse the particles 216 to a larger treatment surface 11. The flow convergent section 80 of the nozzle 12 can be configured to build up pressure in the nozzle 12 so as to accelerate the pressurized gas 100 and the particles 21 carried or delivered by the pressurized gas 100. The nozzle channel 81 can be part of the gas flow passageway 101.

FIG. 7c illustrates another variation of the elongate portion 79. As illustrated in FIG. 7c, the elongate portion 79 can be a substantially cylindrical tube or conduit. In this variation, the pressurized gas 100 can use the substantially cylindrical nozzle channel 81 to deliver the particles 216 in a uniform manner.

FIG. 7d illustrates another variation of the elongate portion 79. As illustrated in FIG. 7d, the thickness of the nozzle wall 75 surrounding the elongate portion 79 can increase as the elongate portion 79 proceeds from the throat section 84 to the nozzle opening 86. As the thickness of the nozzle wall 75 increases, the shape of the nozzle channel 81 tapers so that the nozzle channel 81 is shaped or configured as an extended cone with a base of the cone at the throat section 84 of the nozzle 12 and the tip of the cone ending at the nozzle opening 86. In this variation, the pressurized gas 100 can deliver a more concentrated dose of the particles 216 to a smaller or more focused treatment surface 11.

FIG. 7e illustrates that the wall thickness 83 of the nozzle wall 75 can vary along the elongate portion 79. For example, the nozzle wall 75 can have a first wall thickness 83a and a second wall thickness 83b. The first wall thickness 83a can be the thickness of the nozzle wall 75 surrounding a portion of the nozzle channel 81 proximal to the throat section 84. The second wall thickness 83b can be the thickness of the nozzle wall 75 surrounding a portion of the nozzle channel 81 proximal to the nozzle opening 86. In this example, the first wall thickness 83a can be greater than the second wall thickness 83b.

The variations in the wall thickness 83, such as the difference in thickness between the first wall thickness 83a and the second wall thickness 83b, can provide a selective dampening or silencing effect to different portions of the nozzle 12 when the delivery device 1 is actuated. For example, as illustrated in FIG. 7e, the first wall thickness 83a can be greater than the second wall thickness 83b to selectively minimize or dampen the sound of the pressurized gas 100 as the pressurized gas 100 flows from the throat section 84 or the expansion chamber 10 into the elongate portion 79 of the nozzle 12.

FIG. 7f illustrates another variation of the elongate portion 79 where the second wall thickness 83b is greater than the first wall thickness 83a. In this variation, the nozzle wall 75 is thicker around the portion of the nozzle channel 81 proximal to the nozzle opening 86. The second wall thickness 83b can be greater than the first wall thickness 83a to selectively minimize or dampen the sound of the pressurized gas 100 flowing out of the nozzle 12 or the delivery port 30. The nozzle wall 75 can be thicker around the nozzle opening 86 to reinforce the noise dampening effect of the silencer 5.

FIG. 7g illustrates that a radially inner surface of the nozzle wall 75 can have a coarse surface texture 89 along a portion of the inner surface. The coarse surface texture 89 of the inner nozzle wall 75 can trap or impede the gas molecules comprising the pressurized gas 100. The nozzle wall 75 can also have a smooth radially inner surface along different segments of the nozzle 12. The smooth inner surface of the nozzle wall 75 can accelerate the pressurized gas 100 faster than the portions of the nozzle 12 covered by coarse surface texture 89.

For example, as illustrated 7g, the nozzle wall 75 proximal to the throat section 84 can have a smooth inner wall surface to accelerate the pressurized gas 100 entering the nozzle 12 from the expansion chamber 10. In this example, the inner surface of the nozzle wall 75 proximal to the nozzle opening 86 can have the coarse surface texture 89 to decelerate or slow down the speed of the pressurized gas 100 as the pressurized gas 100 prepares the exit the nozzle 12 through the nozzle opening 86. Also in this example, the nozzle wall 75 having the smooth inner surface can be thicker than the nozzle wall 75 having the coarse inner surface (or having the coarse surface texture 89) since the speed and the sound attributed to the pressurized gas 100 decreases as the pressurized gas 100 flows toward the nozzle opening 86.

Figure 8A:
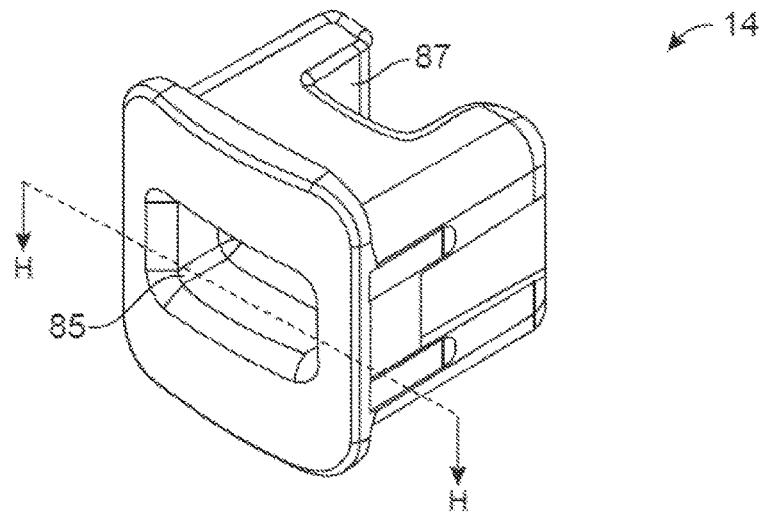
FIG. 8*a* illustrates a variation of a retainer.

FIG. 8a is a perspective view of an example variation of a retainer 14. FIG. 8a illustrates that the retainer 14 can hold or secure the nozzle 12 in place in the delivery device 1. The delivery device 1 can have one, two, or more retainers 14 to hold or secure the nozzle 12 in the delivery device 1. The retainer 14 can be made of polycarbonate. The retainer 14 can have a retainer opening 85 and a retainer space 87.

Figure 8B:
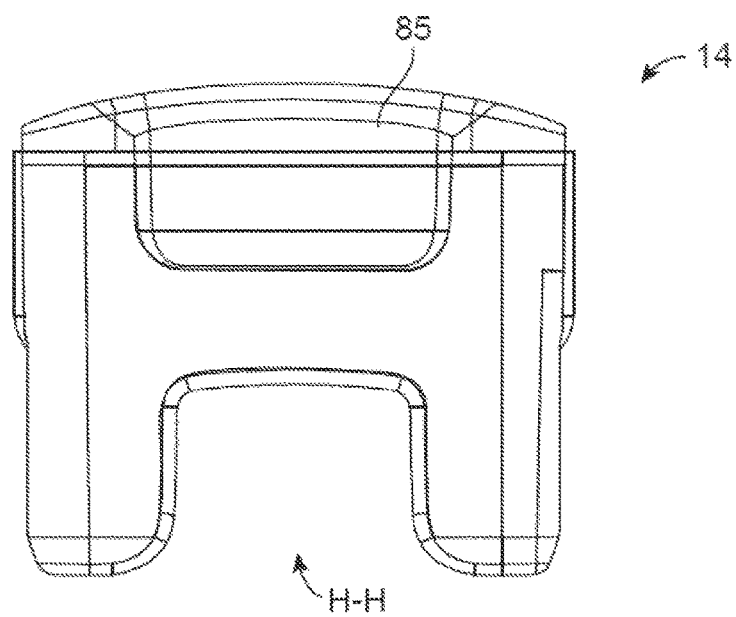

FIG. 8b is a cross-sectional view of an example variation of the retainer 14 of FIG. 8a taken along cross-section H-H. FIG. 8b illustrates that the retainer opening 85 can be coupled or connected to the inner housing 2 of the delivery device 1 and the retainer space 87 can lock or secure the nozzle 12 to the inner housing 2.

Figure 9A:
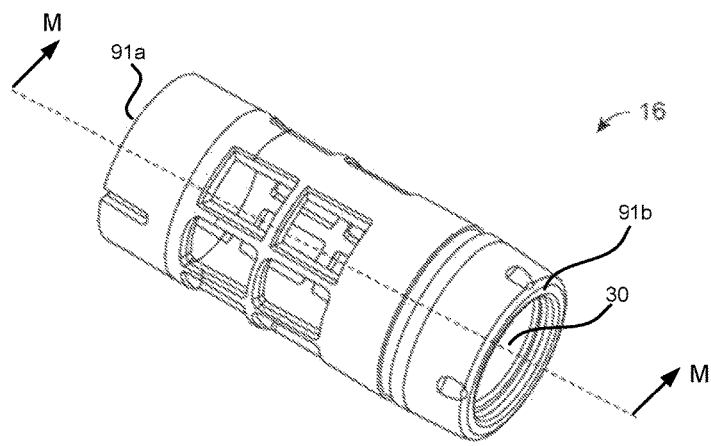
FIG. 9*a* illustrates a variation of a silencer cover.

FIG. 9a is a perspective view of an example variation of the silencer cover 16 of the delivery device 1. The silencer cover 16 can secure or house the silencer packing material 18. The silencer cover 16 and the silencer packing material 18 can combine to form the silencer 5 of the delivery device 1.

FIG. 9a illustrates that the silencer cover 16 can have a silencer upstream end 91a and a silencer downstream end 91b. The silencer upstream end 91a can be coupled or in contact with a portion of the retainer 14, the nozzle 12, the case 22, the inner housing 2, or a combination thereof. In one variation, the silencer downstream end 91b can extend out longitudinally past the case opening 108 of the case 22. When the silencer downstream end 91b extends out past the case opening 108, the silencer downstream end 91b can serve as the injection end 7 of the delivery device 1. In another variation, the silencer downstream end 91b can be encompassed or surrounded by the case 22.

Pressurized gas 100 can flow or move from the silencer upstream end 91a to the silencer downstream end 91b when the delivery device 1 is actuated. The silencer cover 16 can be cylindrical, conical, frustoconical, or any combination thereof. For example, the silencer upstream end 91a can be conical and the silencer downstream end 91b can be frustoconical.

The silencer upstream end 91a and the silencer downstream end 91b can have openings defining the ends of the silencer cover 16. The opening at the silencer downstream end 91b can also serve as the delivery port 30. The silencer cover 16 can be made of or manufactured using a polymer, a metal, or a composite thereof. For example, the silencer cover 16 can be made of or manufactured using high impact polystyrene, polyurethane, or any combination thereof.

The space defined or encompassed by the silencer cover 16, the silencer packing material 18, or a combination thereof can be part of the gas flow passageway 101. For example, the space encompassed by the silencer packing material 18 in between the silencer upstream end 91a and the silencer downstream end 91b can be part of the gas flow passageway 101.

Figure 9B:
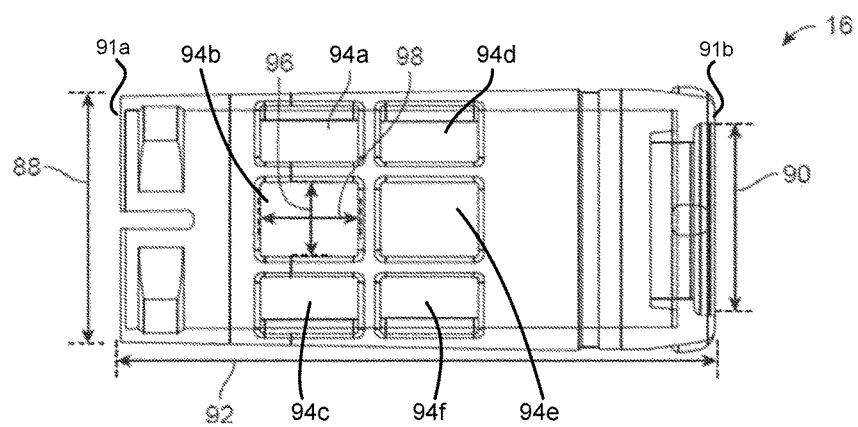

FIG. 9b is a cross-sectional view of an example variation of the silencer cover 16 taken along cross-section M-M. FIG. 9b illustrates that the silencer cover 16 can have a silencer cover outer diameter 88, a silencer cover inner diameter 90, a silencer cover length 92, one or more silencer windows 94, a silencer window width 96, a silencer window length 98, or any combination thereof. The silencer cover 16 can have one, two, three, four, five, or more silencer windows 94.

The silencer cover outer diameter 88 can be between about 25 mm and 35 mm or, more narrowly, between about 25 mm and 30 mm. For example, the silencer cover outer diameter 88 can be about 29 mm or about 30 mm. The silencer cover inner diameter 90 can be between about 15 mm and 20 mm or, more narrowly, between about 16 mm and 18 mm. For example, the silencer cover inner diameter 90 can be about 17 mm.

The silencer cover length 92 can be between about 50 mm and 100 mm or, more narrowly, between about 60 mm and 70 mm. For example, the silencer cover length 92 can be about 64 mm, about 64.6 mm, or about 65 mm. The silencer window width 96 can be between about 5 mm and 10 mm or, more narrowly, between about 6 mm and 9 mm. For example, the silencer window width 96 can be about 7 mm or about 8 mm. The silencer window length 98 can be between about 5 mm and 15 mm or, more narrowly, between about 8 mm and 12 mm. For example, the silencer window length 98 can be about 10 mm, about 11 mm, or about 12 mm. The volume of the silencer cover 16 can be greater than the volume of the expansion chamber 10, the volume of the nozzle 12, or a combination thereof.

The silencer windows 94 (e.g., ports or open cells) can be located radially around the circumferential surface of the silencer cover 16. The silencer windows 94 can allow a portion of the pressurized gas 100 to vent or escape when the pressurized gas 100 is flowing through the silencer 5. The silencer windows 94 can be perforations, openings, or fenestrations shaped as circles, ovals, squares, rectangles, oblong segments, diamonds, waves, or any combination thereof. The silencer windows 94 can each be covered by one or more of the filters 8.

The first silencer window 94a, the second silencer window 94b, the third silencer window 94c, or a combination thereof can be arranged in a first circumferential alignment perpendicular to the device longitudinal axis 32 and around a circumference of the silencer cover 16. The fourth silencer window 94d, the fifth silencer window 94e, the sixth silencer window 94f, or a combination thereof can be arranged in a second circumferential alignment parallel to the first circumferential alignment and also perpendicular to the device longitudinal axis 32.

In one variation, the first circumferential alignment of silencer windows 94 can be diametrically opposed to the second circumferential alignment of silencer windows 94. In another variation, the first circumferential alignment of silencer windows 94 can be adjacent or overlapping with the second circumferential alignment of silencer windows 94.

Two silencer windows can be located on diametrically opposed surfaces or sections of the silencer cover 16 to create a lateral flow channel. The lateral flow channel can allow the pressurized gas 100 to flow laterally out of the silencer cover 16 or silencer 5 from different sides of the silencer cover 16 or silencer 5. The silencer cover 16 can have one, two, three, four, five, or more rows or columns of silencer windows 94. The number of silencer windows 94, the number of rows, the formation of the silencer windows 94, the length or height of the silencer windows 94, or any combination thereof can minimize the sound when the delivery device 1 is actuated. The number of silencer windows 94, the arrangement of silencer windows 94, the length or height of the silencer windows 94, or any combination thereof can also decrease or increase the velocity of the pressurized gas 100 or the particles 216 flowing through the silencer 5.

Figure 9C:
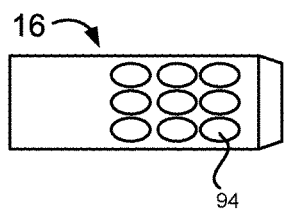
FIGS. 9*c* through 9*h* illustrate variations of the silencer cover.
Figure 9D:
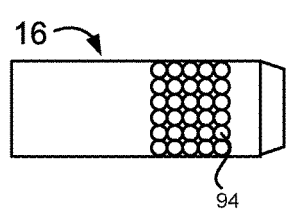
Figure 9E:
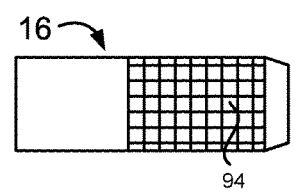

FIGS. 9*c*, 9*d*, and 9*e* illustrate that the silencer cover 16 can be covered, encompassed, or ringed by differently shaped silencer windows 94. For example, FIG. 9*c* illustrates that the silencer windows 94 can be oval shaped. Also, for example, FIG. 9*d* illustrates that the silencer windows 94 can be circular shaped. Moreover, FIG. 9*e* illustrates that the silencer windows 94 can be shaped as squares or be in a mesh configuration. Although not shown in FIGS. 9*c* to 9*e*, the silencer windows 94 can be shaped as diamonds, polygons, sinusoidal openings or slits, or any combination thereof.

Figure 9F:
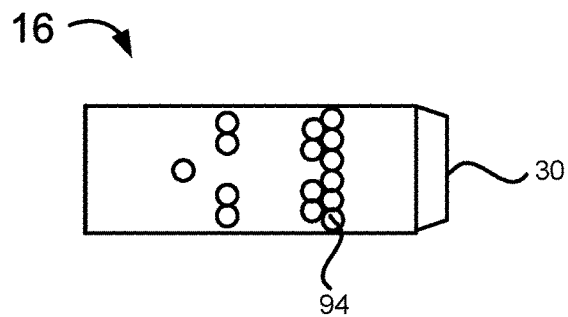

FIG. 9*f* illustrates one example arrangement of the silencer windows 94 around the circumferential surface of the silencer cover 16. For example, FIG. 9*f* shows that the silencer windows 94 can be less concentrated at the silencer upstream end 91*a* and more concentrated at the silencer downstream end 91*b*. Such a configuration can allow the pressurized gas 100 to maintain or increase its velocity and the velocity of the particles 216 when the pressurized gas 100 or the particles 216 first enter the silencer 5 and decrease the velocity of the pressurized gas 100 or the particles 216 as the pressurized gas 100 and the particles 216 flow down the body of the silencer 5. Such a configuration can also minimize or dampen the sound emitted by the delivery device 1 near the device delivery opening 30 when the delivery device 1 is actuated.

Figure 9G:
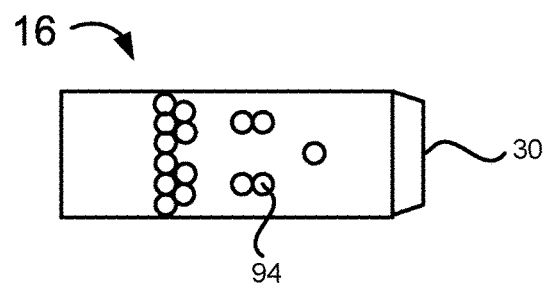

FIG. 9*g* illustrates another example arrangement of the silencer windows 94 around the circumferential surface of the silencer cover 16. For example, FIG. 9*g* shows that the silencer windows 94 can be more concentrated at the silencer upstream end 91*a* and less concentrated at the silencer downstream end 91*b*. This configuration can allow the silencer 5 to increase the velocity of the pressurized gas 100, the particles 216, or a combination thereof as the pressurized gas 100, the particles 216, or a combination thereof flows or travels down the body of the silencer 5.

Figure 9H:
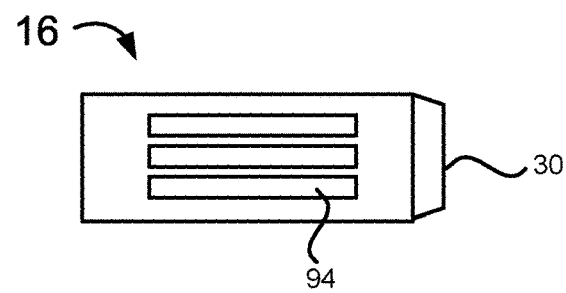

FIG. 9*h* illustrates that the silencer windows 94 can be rectangular windows or perforations parallel to each other and the device longitudinal axis 32. These rectangular windows can be located in between the silencer upstream end 91*a* and the silencer downstream end 91*b*.

Figure 10:
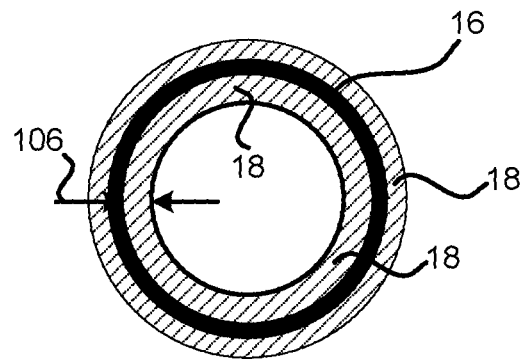

FIG. 10 illustrates a cross-sectional view of an example variation of the silencer 5. FIG. 10 illustrates that the silencer packing material 18 can cover or encompass a radially outer surface of the silencer cover 16. FIG. 10 also illustrates that the silencer packing material 18 can cover or encompass a radially inner surface of the silencer cover 16. The silencer packing material 18 can attach to the inner surface of the silencer cover 16 by an adhesive. The silencer packing material 18 can dampen or reduce the noise emitted or produced by delivery device 1 when the delivery device 1 is actuated. The silencer packing material 18 can be composed of a foam or foam like material. The silencer packing material 18 can be composed of foam comprising porous polyurethane.

The silencer packing material 18 can be injection molded on to the silencer cover 16. The silencer packing material 18 can be double-injection molded so that a second polymer layer is injected over a first polymer layer. The silencer packing material 18 can also be injected into the silencer cover 16. The silencer packing material 18 can be injected into the silencer cover 16 to cover or encompass the radially inner surface of the silencer cover 16. The silencer packing material 18 can be injected into the one or more silencer windows 94. The silencer packing material 18 injected into or on the silencer cover 16 can be heat cured and allowed to cool to solidify the silencer packing material 18. The curing can be performed by UV exposure, air or gas exposure, or a combination thereof. The silencer cover 16 can also be produced by injection molding.

The silencer packing material 18 can also be spray coated onto the radially inner or outer surfaces of the silencer cover 16. The silencer packing material 18 can be formed from one solid piece of flexible or rigid foam die-cut from a larger piece of solid foam. The silencer packing material 18 can be made of other types of polymers including other types of urethanes or thermoplastics.

The case 22 can have a silencer cavity configured to hold the silencer cover 16, the silencer packing material 18, or a combination thereof. The silencer cavity can be defined by an outer surface of the silencer cover 16. A solid foam serving as the silencer packing material 18 can be slidably inserted into the silencer cavity. The solid foam can be inserted into the silencer cavity and flexibly deformed when inside the silencer cavity. The silencer cavity can, for example, be closed on all sides except for an intake port to receive a liquid precursor of the silencer packing material 18 and an outlet port to vent pressure when the silencer packing material 18 is injected into the silencer cavity.

The silencer packing material 18 can cover or surround a portion of the outer radial or circumferential surface of the nozzle 12, the expansion chamber 10, the cassette housing 204, or a combination thereof. For example, the silencer packing material 18 can cover the outer wall 77*b* of the nozzle 12.

The silencer packing material 18 can also surround, cover, or encompass the inner radial surface of the nozzle 12, the expansion chamber 10, or a combination thereof. For example, the silencer packing material 18 can also be coated onto the inner wall 77*a* of the nozzle 12. The silencer packing material 18 can also be placed between the inner wall 77*a* and the outer wall 77*b* of the nozzle 12.

The silencer packing material 18 can have a silencer packing width 106 or thickness. The silencer packing width 106 can be between about 0.01 mm and 2 mm. For example, the silencer packing width 106 can be about 1.8 mm.

The silencer 5, including the silencer packing material 18, can act as a vibration dampener and sound barrier for a portion of the delivery device 1. The silencer packing material 18 can minimize the noise or sound produced when the delivery device 1 is actuated. The pores of the polyurethane forming the silencer packing material 18 can allow a portion of the pressurized gas 100 to escape after the delivery device 1 is actuated. The pores in the silencer packing material 18 can be circular, square, rectangle, diamond, oval, triangular, or any combination thereof. The escape of the pressurized gas 100 through the pores of the silencer packing material 18 can reduce the build-up of gas pressure in portions of the delivery device 1 such as the nozzle 12, the expansion chamber 10, the silencer 5, or a combination thereof. The silencer packing width 106 can be greater than the width of the nozzle wall 75, the width of the expansion chamber 100 wall, or a combination.

The delivery device 1 can emit a sound of around 85 dB when the silencer packing material 18 covers the inside or outside surface of a device segment of the delivery device 1 such as a portion of the nozzle 12, the expansion chamber 10, the silencer cover 16, or a combination thereof.

Figure 11:
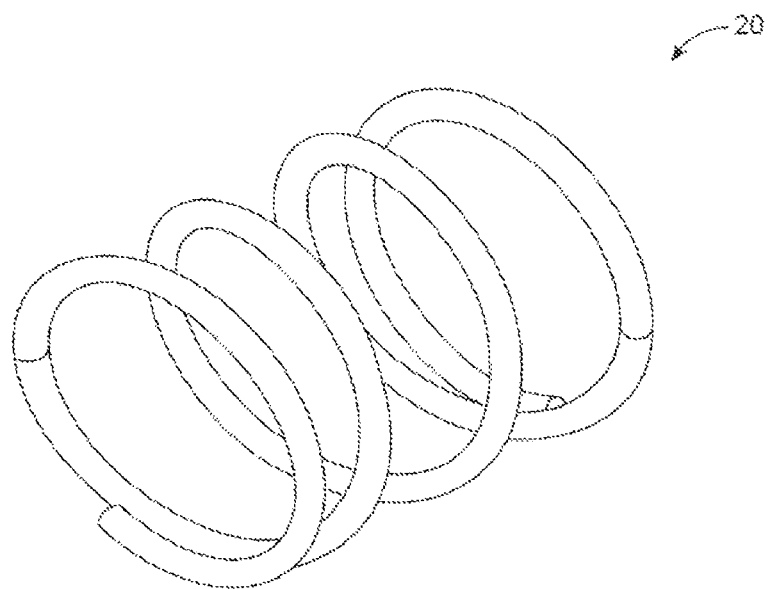

FIG. 11 is a perspective view of an example variation of the spring 20. The spring 20 can be located at the handle end 3 of the delivery device 1. The spring 20 can be coupled to the housing tip 52 at one end of the spring 20 and be coupled with the inner housing 2 at the other end of the spring 20.

The spring 20 can be a substantially helical spring. The spring 20 can be a metallic spring, a polymer-based spring, a shape memory spring such as a Nitinol spring, or any combination thereof. For example, the spring 20 can be made of nickel coated stainless steel. When the delivery device 1 is in an unactuated or resting configuration, the spring 20 can bias, expand, or apply a spring force to the inner housing 2 of the delivery device 1. When the spring 20 applies the spring force to the inner housing 2, the inner housing 2 can then bias, press, or force the trigger 24 in the direction of the safety interlock 114. The safety interlock 114 can be engaged when the trigger seat 208 of the trigger 24 contacts an impeding element of the safety interlock 114 such as the triangular impeding element 29, the notch 15, the latch 17, or any combination thereof. The spring 20 can keep the safety interlock 114 engaged with the trigger 24 by biasing or applying the spring force to the inner housing 2 in the direction of the injection end 7 or the delivery port 30.

In one variation, the safety interlock 114 can be disengaged or unlocked when the inner housing 2 is translated in the direction of the handle end 3. The inner housing 2 can be translated in the direction of the handle end 3 when the silencer cover 16 or the case 22 of the delivery device is pressed against the treatment surface 11. During this translation process, the user can be holding the case 22 of the delivery device 1 with one hand. The user can translate the inner housing 2 in the direction of the handle end 3 by placing the silencer cover 16 or the case 22 on the treatment surface 11 and pushing or pressing the case 22 in the direction of the treatment surface 11. The spring 20 can be compressed when the inner housing 2 is biased or forced in the direction of the handle end 3 of the delivery device 1. The safety interlock 114 can also be disengaged or unlocked when the case 22 is translated in the direction of the treatment surface 11 by the user. The safety interlock 114 can be disengaged or unlocked when the impeding element of the safety interlock 114 translated in the direction of the treatment surface 11 along with the case 22 and the trigger 24 becomes unimpeded or unhindered by the impeding element.

Figure 12A:
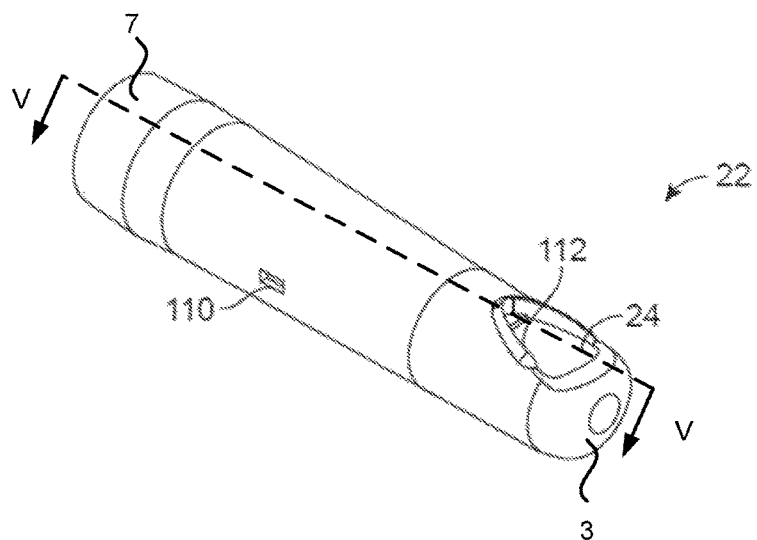

FIG. 12*a* is a perspective view of an example variation of the case 22. FIG. 12*a* illustrates that the case 22 can be the external shell of the delivery device 1. The case 22 can allow a user to actuate the delivery device 1 with one hand. The case 22 can allow the user to actuate the delivery device 1 by holding the handle end 3 of the delivery device 1 with one hand and directing the injection end 7 of the delivery device 1 at the treatment surface 11. For example, in one variation, the user can cover a portion of the treatment surface 11 with the silencer cover 16 or an end of the case 22 distal to the handle end 3. In another variation, the user can hover the silencer cover 16 over the treatment surface 11 without physically contacting the treatment surface 11.

The user can then push the case 22 or apply a longitudinal force to the case 22 toward the treatment surface 11. The user can push the case 22 using the same hand of the user holding the case 22. Concurrent with pushing the case 22, the inner housing 2 of the delivery device 1 can translate in a longitudinal direction opposite or away from the treatment surface 11 or the pushing force. This translation of the inner housing 2 can disengage of the safety interlock 114 to permit the user to actuate the trigger 24. The user can actuate the trigger 24 using one or more fingers of the hand holding the case 22. The user can actuate the trigger 24 by depressing the trigger 24 radially inward toward the device longitudinal axis 32.

As illustrated in FIG. 12*a*, the handle end 3 of the case 22 can be ergonomically designed to allow the user to hold the case 22, press the case 22, and actuate the trigger 24 using one hand. The case 22 can be shaped as a pen. The diameter of the case 22 can be tapered radially inward from the injection end 7 to the handle end 3. The case 22 can be manufactured or composed of high impact polystyrene. The case 22 can be free of edges.

The case 22 can have a protective ridge or rim surrounding a portion of the trigger 24. The protective ridge or rim can be a V-shaped ridge 112 as illustrated in FIG. 12*a*. The protective ridge or rim can prevent accidental actuation of the trigger 24.

Figure 12B:
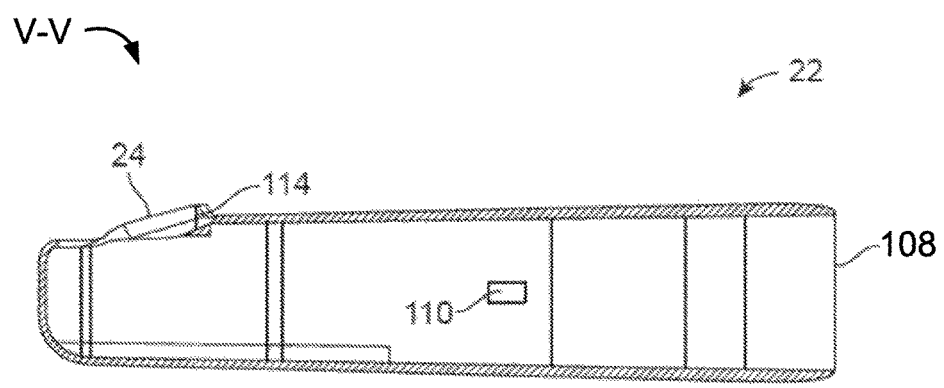
Figure 13A:
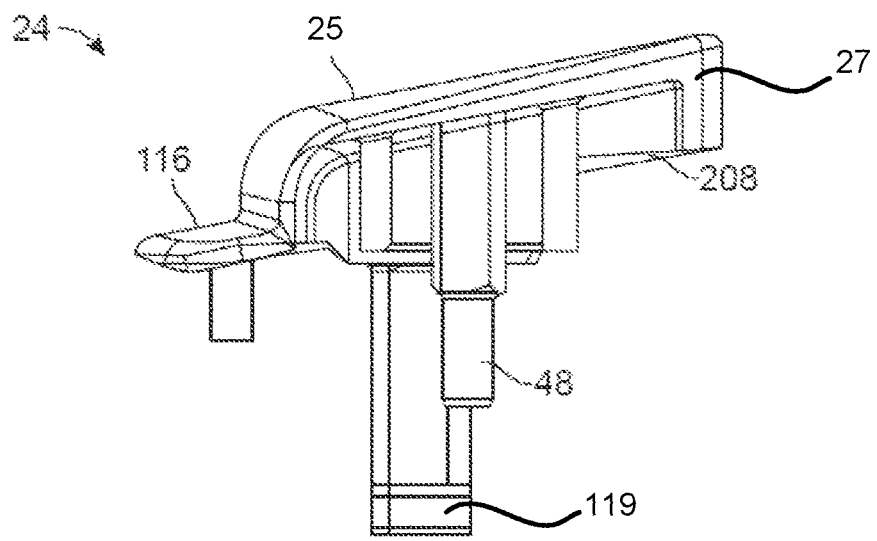
Figure 13B:
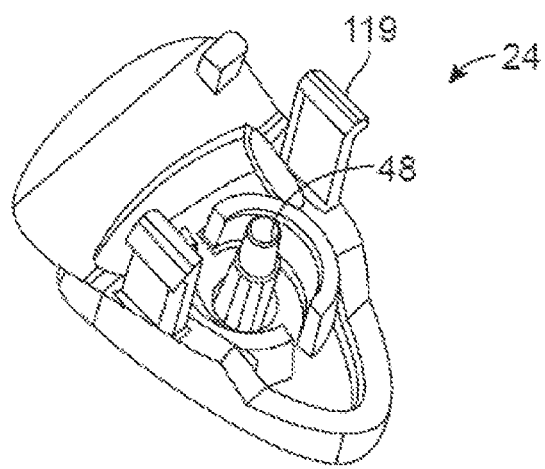

FIG. 12*b* is a cross-sectional view of an example variation of the case 22 taken along cross-section V-V. FIG. 12*b* illustrates that the case 22 can have a case side opening 110 and a case opening 108. The case opening 108 can allow a portion of the silencer cover 16 to extend out of the case 22. The case side opening 110 can be located on a side or circumferential surface of the case 22. The case side opening 110 can act as a vent or port for relieving some of the pressurized gas 100 from the nozzle 12, the expansion chamber 10, the particle cassette 200, or a combination thereof. The case side opening 110 can prevent gas pressure from being built up inside the case 22 beyond a predetermined pressure threshold. For example, the case side opening 110 can prevent the gas pressure inside the case 22 from exceeding 40 bar of pressure, 50 bar of pressure, or 100 bar of pressure.

FIG. **13*a* is a side cross-sectional view of an example variation of the trigger 24. FIG. 13*a* illustrates that the trigger top 27 can be sloped or angled relative to the device longitudinal axis 32. FIG. 13*a* also illustrates that the trigger pin 48 can be coupled or affixed directly underneath the user contact surface 25. The portion of the user contact surface 25 distal to the stepped-down portion 116 of the trigger 24 can be flush or approximately level with the V-shaped ridge 112 (see FIG. 12*a*) of the case 22**.

FIG. **13*b* is a perspective view of an example variation of an underside or radially inward side of the trigger 24 of FIG. 13*a*. FIG. 13*b* illustrates that the trigger 24 can have one or more catches 119 extending from the underside or radially inward side of the trigger 24. The one or more catches 119 can catch onto or engage with an inner surface feature of the inner housing 2, the case 22, or a combination thereof to prevent the trigger 24 from separating from the remainder of the delivery device 1. The distal ends of the catches 119 can be curved or hooked to allow the catches 119 to catch onto or engage with the inner housing 2, the case 22**, or a combination thereof.

FIG. **14*a* is a perspective view of an example variation of the particle cassette 200. FIG. 14*a* illustrates that the particle cassette 200 can have a cassette housing 204 and one or more cassette ports 213. The cassette housing 204 can be substantially cylindrical as shown in FIG. 14*a***. In other variations, the cassette housing 204 can be conical, frusto-conical, cuboidal, or a combination thereof.

The cassette housing 204 can have a cassette housing width 212 and a cassette housing height 214. The cassette housing width 212 can be about 5.00 mm to about 15.0 mm. The cassette housing width 212 can also be about 10.0 mm to about 12.5 mm. For example, the cassette housing width 212 can be about 11.0 mm or 11.1 mm. The cassette housing width 212 can be a diameter of the cassette housing 204 when the cassette housing 204 is substantially cylindrical or conical. The cassette housing 204 can have multiple cassette widths 212 when the cassette housing 204 is frustoconical.

The cassette housing height 214 can be a thickness of the cassette housing 204 along a longitudinal axis of the cassette housing 204. The cassette housing height 214 can be from about 2.00 mm to about 5.00 mm or, more narrowly, from about 3.50 mm to about 4.00 mm. For example, the cassette housing height 214 can be about 3.79 mm or about 4.00 mm.

The cassette ports 213 can be openings defined by the cassette housing 204. For example, when the cassette housing 204 is a cylinder, the cassette ports 213 can be the openings at the ends of the cylinder. The cassette housing 204 can have at least two cassette ports 213. For example, the cassette housing 204 can have a cassette port 213 at a first end of the cassette housing 204 and another cassette port 213 at a second end of the cassette housing 204. The first end of the cassette housing 204 can be an upstream end of the cassette housing 204 and the second end of the cassette housing 204 can be a downstream end of the cassette housing 204.

The cassette housing 204 can be housed or secured by the expansion chamber 10. For example, the cassette housing 204 can be housed or secured by the cassette holding portion 69 of the expansion chamber 10. In another variation, the cassette housing 204 can be coupled or in contact with the expansion chamber 10 at the first or upstream end of the cassette housing 204 and coupled or in contact with the nozzle 12 at the second or downstream end of the cassette housing 204. For example, the cassette port 213 at the first or upstream end of the cassette housing 204 can be coupled to, in fluid communication with, or aligned with the second chamber opening 70b of the expansion chamber 10 and the cassette port 213 at the first or downstream end of the cassette housing 204 can be coupled to, in fluid communication with, or aligned with the flow convergent section 80 of the nozzle 12.

The cassette housing 204 can be made of a polymer, a metal, or a composite thereof. The cassette housing 204 can be made of a high molecular weight polymer resin. The cassette housing 204 can be made of a copolymer such as ethylene vinyl acetate (EVA). The cassette housing 204 can be made of an EVA copolymer comprising monomers of ethylene and vinyl acetate (VA). The cassette housing 204 can be made of an EVA copolymer with about 18% to about 28% by weight of VA and the remainder being ethylene. The cassette housing 204 can also be made of an EVA copolymer with about 18% to about 20% by weight of VA and the remainder being ethylene. The cassette housing 204 can also be made of an EVA copolymer with about 18% by weight of VA and about 82% by weight of ethylene.

The weight percent of VA in the EVA copolymer used to make the cassette housing 204 is an important factor in the construction of the delivery device 1. As the VA weight percentage increases relative to ethylene, the VA disrupts the polyethylene crystallinity, which ca lower the melting point, modulus, and hardness of the cassette housing 204. The weight percentage of VA in the EVA copolymer can also make the copolymer more polar, which can improve the adhesive properties of the copolymer to polar substrates such as films or membranes. For example, the cassette housing 204 can be made of an EVA copolymer with about 18% to about 28% by weight of VA in order to improve the adhesion of the cassette housing 204 to a cassette membrane 210 (see FIGS. 14b-14d).

The cassette housing 204 can also be made of an EVA copolymer with a low melt index. The cassette housing 204 can also be made of an EVA copolymer with a low melt index and a high softening temperature or ring and ball temperature. The cassette housing 204 can be made of a low melt index EVA copolymer with about 18% to about 28% by weight of VA. The cassette housing 204 can be made of a low melt index EVA copolymer with about 18% to about 28% by weight of VA and a high softening temperature.

Table 1 below lists thermal properties of low melt index EVA copolymers of different VA compositions. The softening temperature or ring and ball temperature of a high molecular weight polymer resin can be a reflection of the differential scanning calorimetry melting point and the polymer viscosity. For example, as indicated in Table 1, an EVA copolymer resin can have a VA percentage of about 18% to about 28% by weight, a melting point of about 67° C. to about 75° C., and a softening temperature or ring and ball temperature of about 110° C. to about 171° C.

The cassette housing 204 can be made of an EVA copolymer with about 18% by weight of VA, a melting point of between 60° C. and 80° C., a softening temperature of above 100° C., and a freezing point of between 40° C. and 50° C.

The cassette housing 204 can also be made of an EVA copolymer with about 28% by weight of VA, a melting point of between 60° C. and 80° C., a softening temperature of above 100° C., and a freezing point of between 40° C. and 50° C.

The cassette housing 204 can be made of an EVA copolymer between about 18% to about 28% by weight of VA and with a melting point of between 60° C. and 80° C., a softening temperature of above 100° C., and a freezing point of between 40° C. and 50° C.

TABLE 1

Thermal Properties of Low Melt Index EVA Copolymers

| % Vinyl Acetate (weight) | Melt Index (decigram/min) | Melt Point (° C.) | Softening Temp. (Ring and Ball Temp.) (° C.) |
| --- | --- | --- | --- |
| 40 | 57 | 47 | 104 |
| 32 | 43 | 63 | 110 |
| 28 | 3 | 75 | 171 |
| 28 | 43 | 74 | 110 |
| 18 | 2.5 | 67 | 188 |
| 12 | 2.5 | 74 | 199 |
| 9 | 2 | 81 | 193 |

Table 2 below lists thermal properties of high melt index EVA copolymers of different VA compositions. As indicated in Table 2, EVA copolymers with a high melt index can have a low softening temperature.

| % Vinyl Acetate (weight) | Melt Index (decigram/min) | Melt Point (° C.) | Freeze Pt. (° C.) | Softening Temp. (Ring and Ball Temp.) (° C.) |
|---|---|---|---|---|
| 28 | 400 | 60 | 39 | 82 |
| 18 | 500 | 73 | 53 | 88 |

The entire particle cassette 200, including the cassette housing 204 and the cassette membrane 210 covering a cassette port 213 of the particle cassette 200, can be heated to a softening temperature at or above 100° C. For example, the entire particle cassette 200 can be heated to a softening temperature between 100° C. and 188° C. Heating the cassette housing 204 and the cassette membrane 210 to between 100° C. and 188° C. can allow the cassette housing 204 to melt and form permanent bonds to the polymers comprising the cassette membrane 210. For example, the EVA copolymer of the cassette housing 204 can bond to the polycarbonate, the polyethylene terephthalate (PET), or the polyether ether ketone (PEEK) of the cassette membrane 210. The particle cassette 200, including the heat sealed cassette housing 204 and the cassette membrane 210, can then be cooled or allowed to cool to below the freezing point of the EVA copolymer to allow the bonds to set. The particle cassette 200 can be cooled to between about 40° C. to about 50° C. The particle cassette 200 can also be cooled to between about 37° C. to about 45° C. The particle cassette 200 can also be cooled to about room temperature or about 37° C.

Figure 14A:
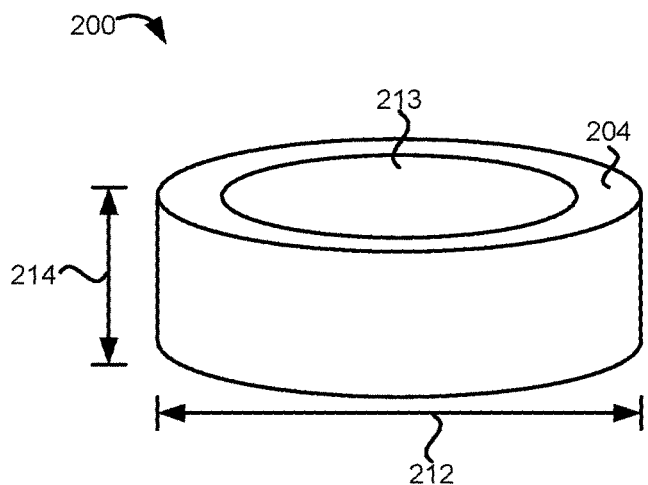
Figure 14B:
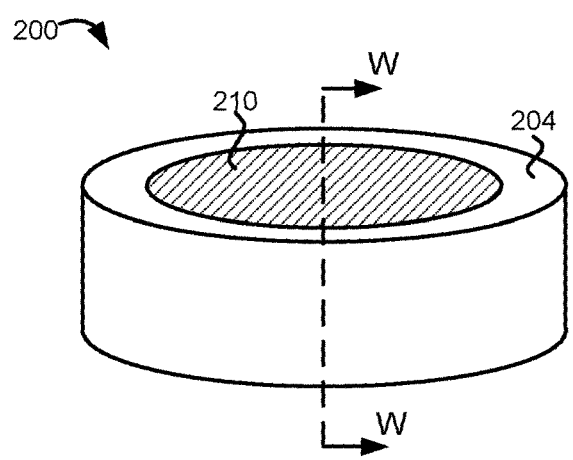

FIG. 14b is a perspective view of another example variation of the particle cassette 200. FIG. 14b illustrates that the particle cassette 200 can have a cassette membrane 210 covering or sealing a cassette port 213 of the particle cassette 200. The cassette membrane 210 can cover one or more cassette ports 213 at the first or upstream end of the cassette housing 204 and one or more cassette ports 213 at the second or downstream end of the cassette housing 204.

The cassette membrane 210 can be a thin layer or film. The cassette membrane 210 can be made of polycarbonate, polyethylene terephthalate (PET), polyether ether ketone (PEEK), or any combination thereof.

In one variation, the cassette membrane 210 can be made from 100% polycarbonate. In another variation, the cassette membrane 210 can be made from 33.3% PET, 33.3% PEEK, and 33.3% polycarbonate. In yet another variation, the cassette membrane 210 can be made from 50% PET or PEEK and 50% polycarbonate. The cassette membrane 210 can also be made from 100% PEEK. The cassette membrane 210 can also be made from 100% PET.

Figure 14C:
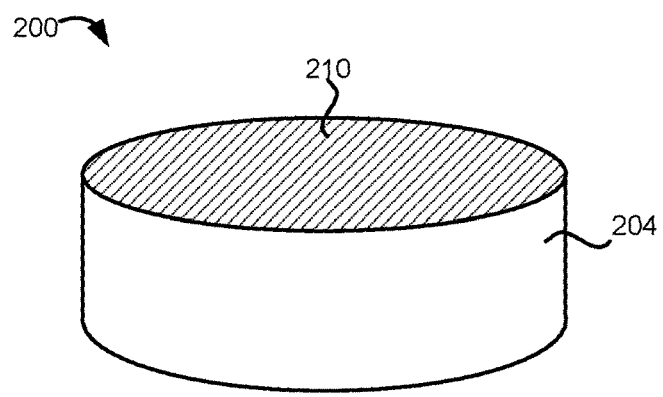

FIG. 14c is a perspective view of another example variation of the particle cassette 200. FIG. 14c illustrates that the cassette membrane 210 can cover or seal the entire end of the cassette housing 204 including the cassette port 213 and the portions of the cassette housing 204 encompassing the circumference of the cassette port 213. The cassette housing 204 can be covered or sealed by the cassette membrane 210 as depicted in FIG. 14c at one end, such as the first or upstream end of the cassette housing 204, and be covered or sealed by the cassette membrane 210 as depicted in FIG. 14b or FIG. 14c at another end, such as the second or downstream end of the cassette housing 204. Covering or sealing more or less of the surface area of the cassette ports 213 or the ends of the cassette housing 204 can alter the burst pressure resistance or membrane strength of the cassette membrane 210. The burst pressure resistance or the membrane strength of the cassette membrane 210 can be the amount of energy or burst pressure needed to puncture or cause a breach in the cassette membrane 210.

The cassette membrane 210 can be breached or punctured when the pressure of the pressurized gas 100 or the energy delivered by the pressurized gas 100 exceeds a predetermined threshold. For example, the pressurized gas 100 can breach or puncture the cassette membrane 210 when the pressure of the pressurized gas 100 exceeds between about 10 bar and 40 bar. In another variation, the pressurized gas 100 can breach or puncture the cassette membrane 210 when the pressure of the pressurized gas 100 exceeds about 40 bar. The pressurized gas 100 can breach or puncture the cassette membrane 210 when the pressure of the pressurized gas 100 is between about 40 bar and 100 bar. The pressurized gas 100 can breach or puncture the cassette membrane 210 when the pressure of the pressurized gas 100 exceeds about 100 bar.

Figure 14D:
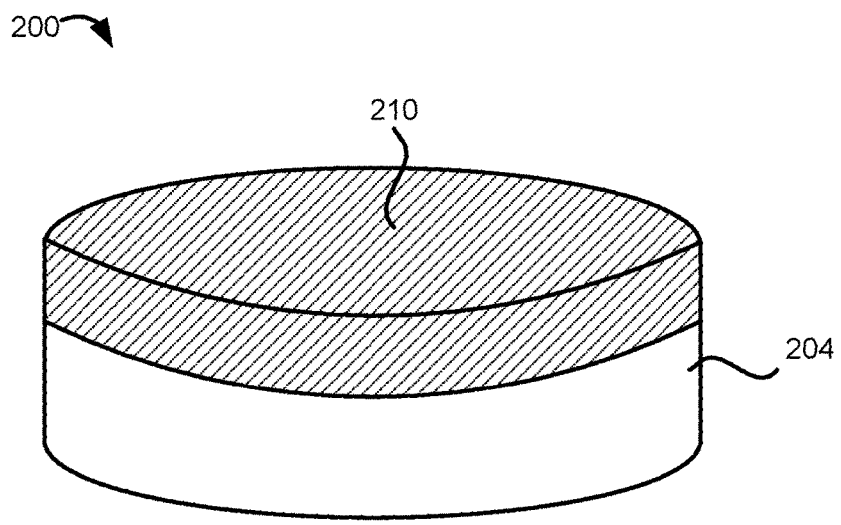

FIG. 14d is a perspective view of another example variation of the particle cassette 200. FIG. 14d illustrates that the cassette membrane 210 can cover or seal the entire end of the cassette housing 204 and a portion of the outer radial wall of the cassette housing 204. For example, the cassette membrane 210 can cover or seal the entire end of the cassette housing 204 and between about 1.00 mm to about 3.00 mm of the radial wall of the cassette housing 204 along the cassette housing longitudinal axis. The cassette housing 204 can be covered or sealed by the cassette membrane 210 as depicted in FIG. 14d at one end, such as the first or upstream end of the cassette housing 204, and be covered or sealed by the cassette membrane 210 as depicted in FIG. 14b, FIG. 14c, or FIG. 14d at another end, such as the second or downstream end of the cassette housing 204.

Figure 14E:
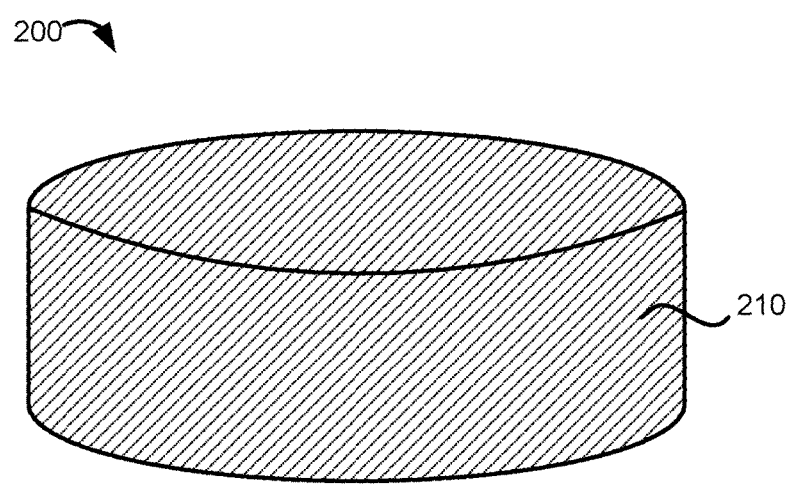

FIG. 14e is a perspective view of another example variation of the particle cassette 200. FIG. 14e illustrates that the cassette membrane 210 can cover or seal the entire cassette housing 204. In this variation, the cassette membrane 210 can act as a wrapper to wrap or seal the entire cassette housing 204. In the variations illustrated in FIGS. 14b to 14e, the cassette membrane 210 can be sealed, adhered, or affixed to the cassette housing 204 by placing the cassette membrane 210 in the desired position or arrangement relative to the cassette housing 204 and heating the cassette membrane 210 and the cassette housing 204 to a softening temperature. The soften temperature can be around 150° C. For example, when the cassette housing 204 is an EVA copolymer of VA and ethylene, the softening temperature can be around 150° C. or more. When heated, the EVA copolymer of the cassette housing 204 can bond to the polymer of the cassette membrane 210, such as the polycarbonate. The heated cassette housing 204 and the cassette membrane 210 can then be cooled or allowed to cool to between about 37° C. to about 50° C. or, more narrowly, between about 40° C. and 50° C.

Figure 14F:
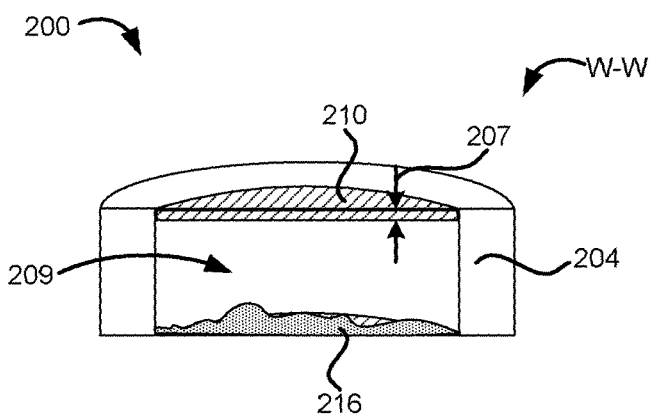

FIG. 14f is a cross-sectional view of a variation of the particle cassette 200 of FIG. 14b taken along cross-section W-W. FIG. 14f illustrates that the cassette housing 204 and the cassette membrane 210 can form a particle reservoir 209. The particle reservoir 209 can be a space or cavity enclosed or encompassed by the cassette housing 204 and the cassette membrane 210. The particle reservoir 209 can be a source of or a resting place for the particles 216. The particles 216 are shown in FIG. 14f as fine grains of powder or particulates.

The particles 216 can be therapeutics including pharmaceuticals, biologics, genetic material, or a combination thereof in particulate or powdered from. The particles 216 can be freeze-dried or lyophilized chemical compounds, molecules, biological material, or a combination thereof.

The particles 216 can be desiccated or encapsulated chemical compounds, molecules, biological material, or a combination thereof. For example, the particles 216 can be powdered Lidocaine or another anesthetic. The particles 216 can also be powdered, desiccated, or lyophilized insulin, epinephrine, adrenaline, or a combination thereof.

When the cassette housing 204 is substantially a cylinder, the particle reservoir 209 can be a smaller cylindrical space enclosed or encompassed by the walls of the cylinder. In one variation, the particle reservoir 209 can have a reservoir diameter of about 4.00 mm to about 10.0 mm. The particle reservoir 209 can also have a reservoir diameter of about 5.00 mm to about 7.00 mm. For example, the reservoir diameter can be about 6.00 mm or 6.10 mm.

The cassette membrane 210 can have a membrane thickness 207. The membrane thickness 207 of the cassette membrane 210 can be about 10.0 microns. The membrane thickness 207 of the cassette membrane 210 can be from about 10.0 microns to about 30.0 microns. The membrane thickness 207 can also be from about 15.0 microns to about 24.0 microns. For example, the membrane thickness 207 of the cassette membrane 210 can be about 15.0 microns, 20.0 microns, or 25.0 microns.

Figure 14G:
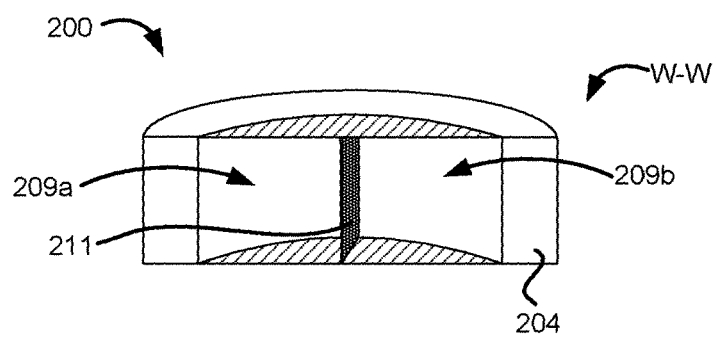

FIG. 14g is a cross-sectional view of another variation of the particle cassette 200 of FIG. 14b taken along cross-section W-W. FIG. 14g illustrates that the particle cassette 200 can have a divider 211 dividing the particle cassette 200 or the cassette housing 204 into two or more particle reservoirs 209. For example, as illustrated in FIG. 14g, the divider 211 can divide the particle cassette 200 into a first particle reservoir 209a and a second particle reservoir 209b. Although two particle reservoirs 209 are shown in FIG. 14g, it is contemplated that multiple dividers 211 can divide up the particle cassette 200 into three, four, five, or more particle reservoirs 209 depending on the combination of therapeutics or pharmaceuticals desired by the treatment.

For example, as illustrated in FIG. 14g, the particle reservoirs 209a and 209b can be halved instances of the particle reservoir of FIG. 14f. The divider 211 can be formed using an extension, divot, or concavity of the cassette housing 204. The divider 211 can also be formed using the same material as the cassette membrane 210. The divider 211 can also have a thickness similar to the membrane thickness 207 of the cassette membrane 210.

Figure 18:
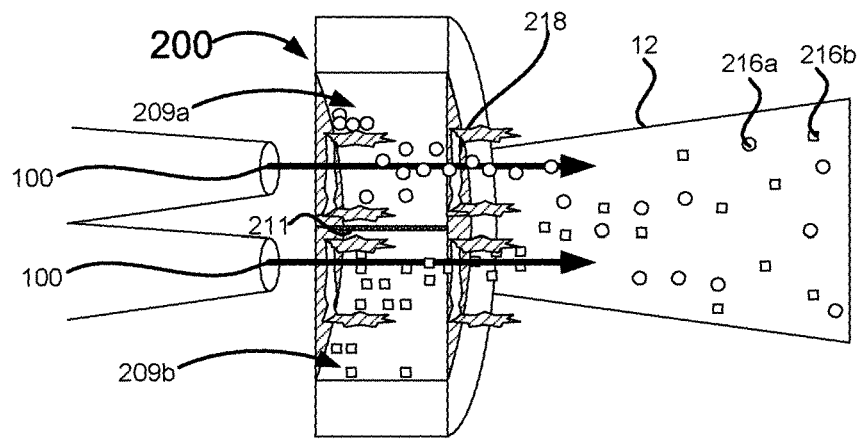
Figure 19A:
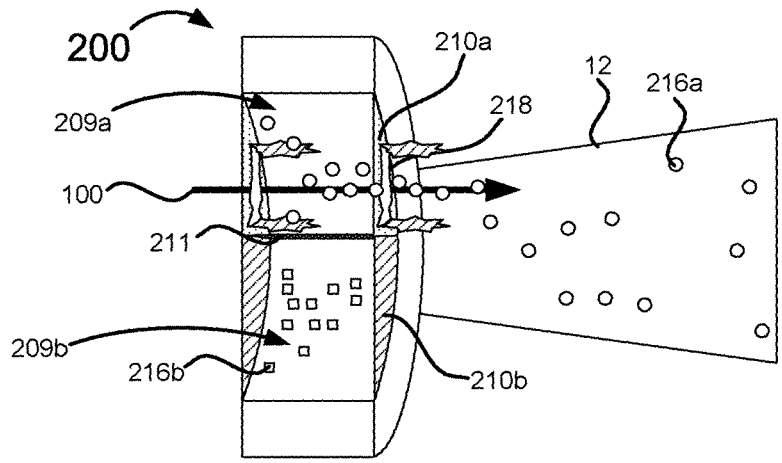
Figure 19B:
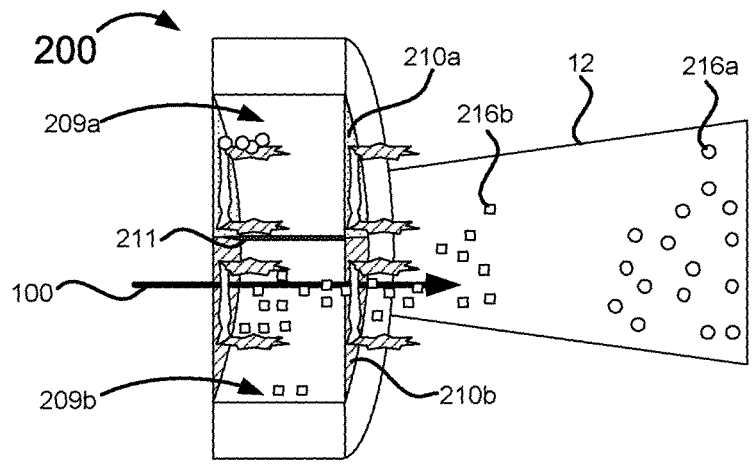
Figure 20:
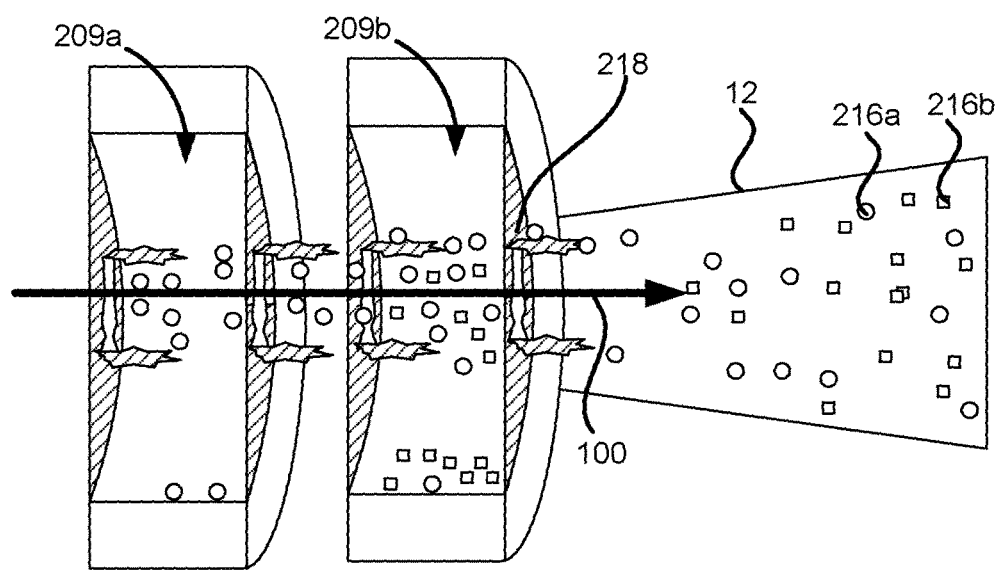

In the example variation shown in FIG. 14g, the first particle reservoir 209a can be used to store and eventually deliver a first-type particle 216a (see FIGS. 18, 19a, and 19b) and the second particle reservoir 209b can be used to store and eventually deliver a second-type particle 216b (see FIGS. 18, 19a, and 19b). The first-type particle 216a and the second-type particle 216b can be different types of therapeutics such as different types of pharmaceuticals, biologics, genetic material, or a combination thereof. For example, the first-type particle 216a can be a lyophilized vaccine and the second-type particle 216b can be a vaccine adjuvant.

Figure 14H:
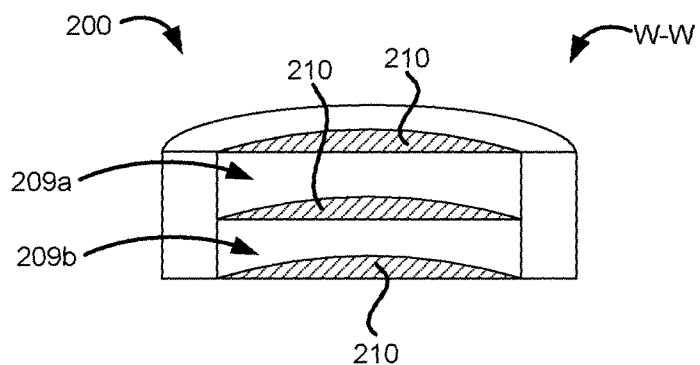

FIG. 14h is a cross-sectional view of another variation of the particle cassette 200 of FIG. 14b taken along cross-section W-W. FIG. 14h illustrates that three instances of the cassette membrane 210 can form another variation of the first particle reservoir 209a and the second particle reservoir 209b. As shown in FIG. 14h, one of the cassette membranes 210 can act as a middle layer dividing the cassette housing 204 along the longitudinal axis of the cassette housing 204. In this variation, the cassette membrane 210 serving as the middle layer or the transverse divider can have a different membrane thickness 207 than the cassette membranes 210 covering or sealing the ends of the cassette housing 204.

In the variation shown in FIG. 14h, the particle cassette 200 can allow the first-type particle 216a to mix with the second-type particle 216b in either the first particle reservoir 209a or the second particle reservoir 209b.

Figure 15A:
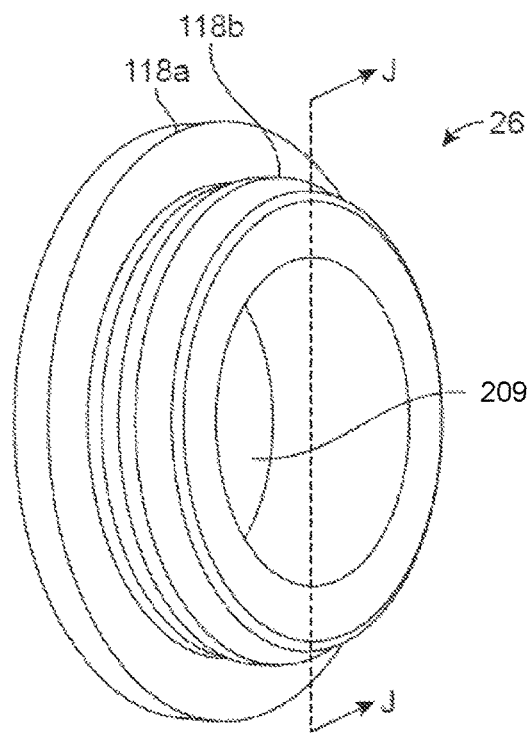

FIG. 15a is a perspective view of a variation of a male cassette part 26 of the particle cassette 200. FIG. 15 illustrates that the male cassette part 26 can have a male base portion 118a and a male thread portion 118b. The male base portion 118a can be covered or sealed by the cassette membrane 210. When the male base portion 118 is covered or sealed by the cassette membrane 210, the particles 216 can then be introduced or placed inside the particle reservoir 209 created by the interior of the male cassette part 26 and the cassette membrane 210.

Figure 15B:
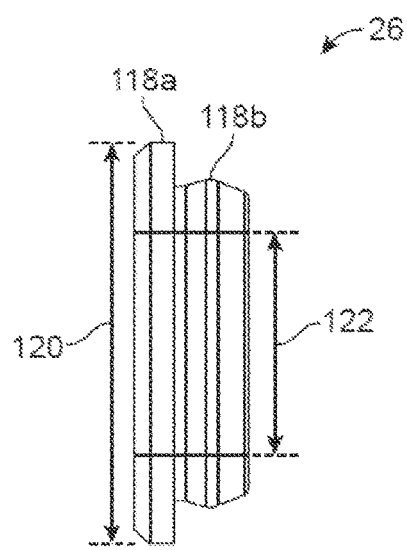

FIG. 15b is a side view of a variation of the male cassette part 26 of the particle cassette 200. FIG. 15 illustrates that the male cassette part 26 can have a male cassette outer diameter 120 and a male cassette inner diameter 122. The male cassette outer diameter 120 can be greater than the male cassette inner diameter 122. In one variation, the male cassette outer diameter 120 can be equivalent to the cassette housing width 212. For example, the male cassette outer diameter 120 can be about 5.00 mm to about 15.0 mm. The male cassette outer diameter 120 can also be about 10.0 mm to about 12.5 mm. For example, the male cassette outer diameter 120 can be about 11.0 mm or 11.1 mm.

The male cassette inner diameter 122 can be equivalent to the reservoir diameter. For example, the male cassette inner diameter 122 can be about 4.00 mm to about 10.0 mm. The male cassette inner diameter 122 can also have a reservoir diameter of about 5.00 mm to about 7.00 mm. For example, the male cassette inner diameter 122 can be about 6.00 mm or 6.10 mm. The male cassette part 26 can be composed of or made from the same material as the cassette housing 204.

Figure 16A:
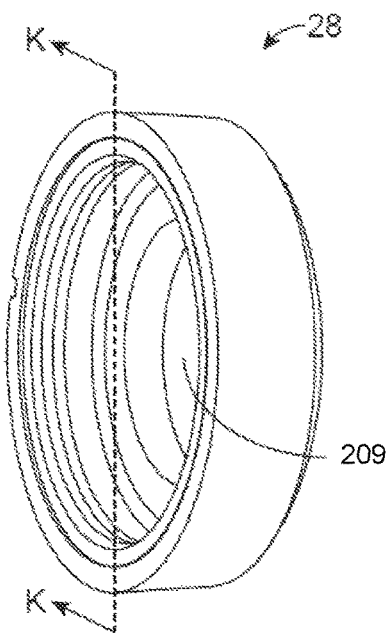

FIG. 16a is a perspective view of a variation of a female cassette part 28 of the particle cassette 200. The male cassette part 26 and the female cassette part 28 can be designed or configured so that the male cassette part 26 can be coupled or screwed into the female cassette part 28. The male cassette part 26 and the female cassette part 28 can combine to form the cassette housing 204. The female cassette part 28 can be made from the same material as the male cassette part 26, the cassette housing 204, or a combination thereof.

Figure 16B:
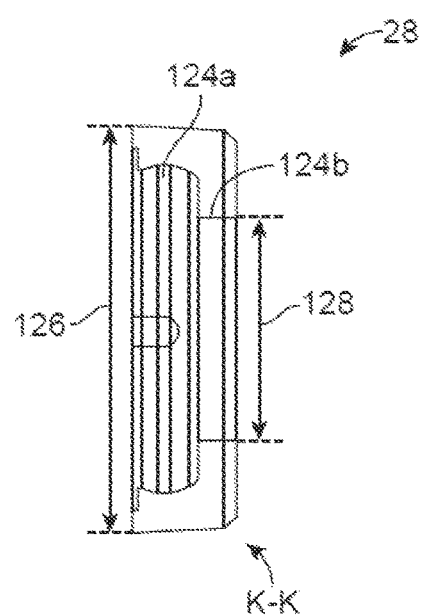

FIG. 16b is a cross-sectional view of a variation of the female cassette part 28 of FIG. 16a taken along cross-section K-K. FIG. 16b illustrates that the female cassette part 28 can have a female thread portion 124a and a female port 124b. The female thread portion 124a can be a receiving thread or a counterpart thread to the male thread portion 118b. The female cassette part 28 can be coupled to the male cassette part 26 by screwing the male thread portion 118b into the female thread portion 124a. The female cassette part 28 can also be heat sealed or coupled through an adhesive to the male cassette part 26 in combination with or in lieu of the thread coupling.

The female port 124b can be one of the cassette ports 213. FIG. 16b illustrates that the female cassette part 28 can have a female cassette outer diameter 126 and a female cassette inner diameter 128. The female cassette outer diameter 126 can be equivalent to the male cassette outer diameter 120 or the cassette housing width 212.

The female cassette inner diameter 128 can be equivalent to the male cassette inner diameter 122 or the reservoir diameter. The female port 124b can be sealed or covered by the cassette membrane 210. When the female port 124b of the female cassette part 28 is covered or sealed by the cassette membrane 210, the female cassette part 28 can be used as a cap to cap off the male cassette part 26 comprising the particles 216 in the particle reservoir 209.

In another variation, particles 216 can be introduced or placed into the reservoir 209 created by the female cassette part 28 and the cassette membrane 210. In this variation, the female cassette part 28 can be screwed on or into the male cassette part 26 comprising additional instances of the particles 216, different types of particles 216, or no particles 216.

The particle cassette 200 can be implemented using the female cassette part 28 and the male cassette part 26 to allow one side or end of the female cassette part 28 and one side or end of the male cassette part 26 to be sealed or covered by the cassette membrane 210. The particles 216 can then be introduced to the particle reservoir 209 in the female cassette part 28, the particle reservoir 209 in the male cassette part 26, or the particle reservoirs 209 in both of the male cassette part 26 and the female cassette part 28 once the heat sealed cassette membrane 210 and cassette parts (the male cassette part 26, the female cassette part 28, or a combination thereof) have cooled from the softening temperature of the polymer used to construct the cassette parts (such as the EVA copolymer) to room temperature or a temperature which is not harmful to the particles 216. Constructing the cassette housing 204 by engaging or coupling the female cassette part 28 with the male cassette part 26 can allow a manufacturer or user of the delivery device 1 to introduce the particles 216 to the particle cassette 200 without subjecting the particles 216 to high temperatures.

Figure 17A:
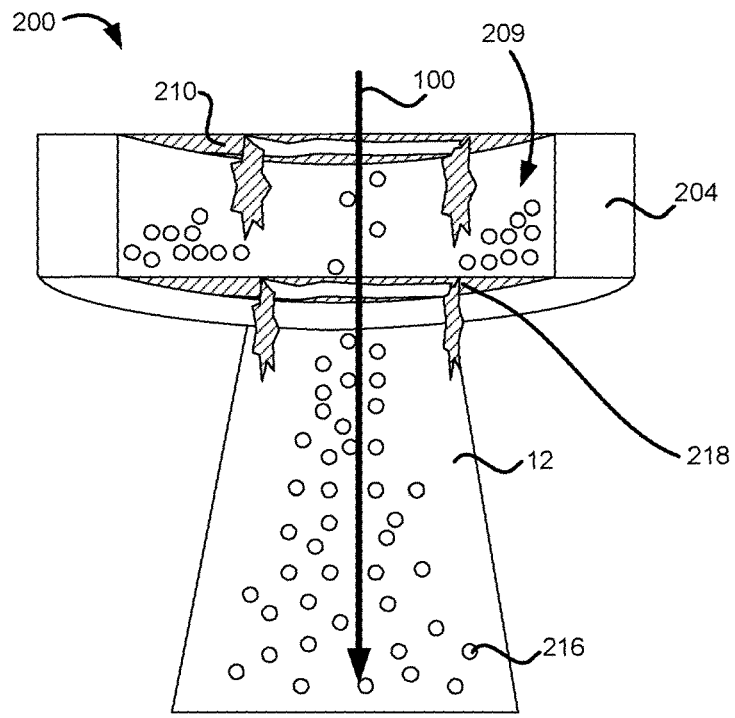

FIG. 17a illustrates that the pressurized gas 100 can breach or burst open the cassette membrane 210 to deliver or propel the particles 216 from the particle reservoir 209 to nozzle 12 and eventually to the treatment surface 11. FIG. 17a illustrates that the pressurized gas 100 can create one or more membrane breaches 218 in the cassette membrane 210 covering the cassette ports 213. The membrane breaches 218 can involve tears, rips, disfiguration, or displacements of the cassette membrane 210. For example, FIG. 17a illustrates that the membrane breach 210 can involve a bifold rupturing of the intact cassette membrane 210. Although not shown in FIG. 17a, it is contemplated that the membrane breach 210 can also involve a circular rupturing, a three-fold rupturing, a four-fold rupturing, or a combination there of the cassette membrane 210.

FIG. 17a illustrates that the particles 216 can be carried by the pressurized gas 100 through the burst cassette membrane 210 out of the particle cassette 200.

It should be understood by one of ordinary skill in the art that the balls and squares used to depict the particles 216 in FIGS. 17a, 17b, 18, 19a, 19b, and 20 are for illustrative purposes only and are not to scale or shaped according to their true geometries.

The pressurized gas 100 can create the membrane breach 218 in the cassette membrane 210 when the pressure of the pressurized gas 100 exceeds a predetermined threshold. For example, the pressurized gas 100 can create the membrane breach 218 in the cassette membrane 210 when the pressure of the pressurized gas 100 exceeds 10 bar. In other variations, the pressurized gas 100 can create the membrane breach 218 in the cassette membrane 210 when the pressure of the pressurized gas 100 exceeds 20 bar, 30 bar, or 40 bar. In yet another variation, the pressurized gas 100 can create the membrane breach 218 in the cassette membrane 210 when the pressure of the pressurized gas 100 exceeds 100 bar. As illustrated in FIG. 17a, when the pressurized gas 100 has created a membrane breach 218 in the cassette membranes 210 covering both the upstream and the downstream ends of the particle cassette 200, the particle reservoir 209 can become part of the gas flow passageway 101.

When the delivery device 1 is actuated, greater than 40% of the particles 216 stored in the particle reservoir 209 can be delivered by the pressurized gas 100 to the treatment surface 11. Moreover, when the delivery device 1 is actuated, between 40-85% of the particles 216 stored in the particle reservoir 209 can be delivered by the pressurized gas 100 to the treatment surface 11. In addition, when the delivery device 1 is actuated, greater than 70% of the particles 216 stored in the particle reservoir 209 can be delivered by the pressurized gas 100 to the treatment surface 11.

The delivery device 1 can deliver particles 216 to the treatment surface 11 at such yields due to the advantages provided by the particle cassette 200 comprising a polycarbonate cassette membrane 210 covering or sealing a cassette housing 204 comprising an EVA copolymer having 18-28% by weight of VA.

Figure 17B:
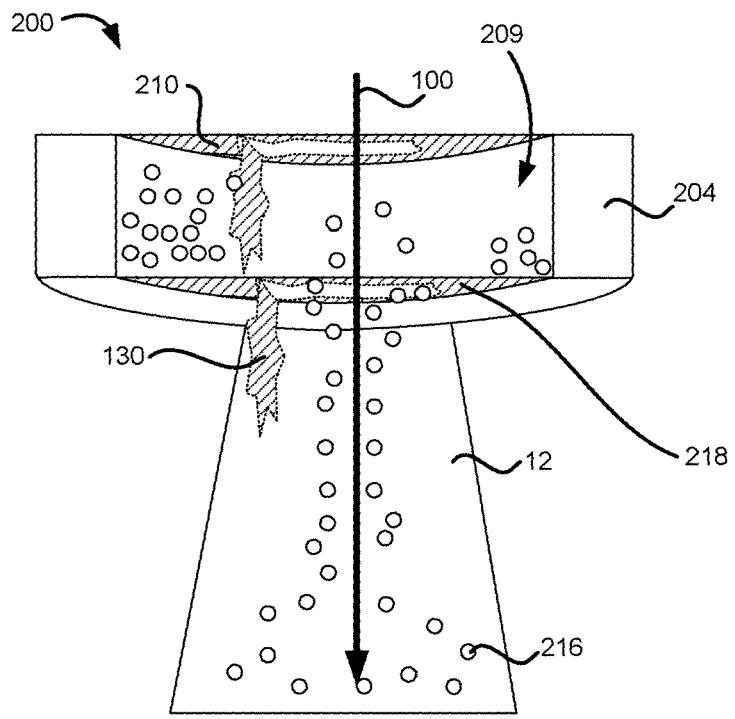

FIG. 17b illustrates that the cassette membrane 210 can have a pre-cut or pre-perforated section 219 which separates when the pressurized gas 100 exceeds a burst pressure. The pre-perforated section 218 can be a part of the cassette membrane 210 and can separate from the remainder of the cassette membrane 210 when in contact with the pressurized gas 100.

The pre-perforated section 219 can have a section diameter. The section diameter can be equivalent to the male cassette inner diameter 122, the female cassette inner diameter 128, or a combination thereof. The section diameter can also be smaller than the male cassette inner diameter 122, the female cassette inner diameter 128, or a combination thereof. The pre-perforated section 218 can be located in the center of the cassette membrane 210. The pre-perforated section 218 can also be located in any part of the cassette membrane 210 in the gas flow passageway 101.

FIG. 18 illustrates that the pressurized gas 100 can create one or more breaches 218 in the cassette membrane 218 covering or sealing the first particle reservoir 209a and the second particle reservoir 209b. In the variation depicted in FIG. 18, the first particle reservoir 209a can comprise the first-type particle 216a and the second particle reservoir 209b can comprise the second-type particle 216b. The two particle reservoirs 209 can be created by the divider 211. The divider 211 can separate the first-type particle 216a from the second-type particle 216b.

Although the variation shown in FIG. 18 shows the divider 211 as staying in tact when the pressurized gas 100 breaches the cassette membrane 210, it is contemplated that the pressurized gas 100 can also breach the divider 211 and the first-type particle 216a can mix with the second-type particle 216b when the divider 211 is breached. The divider 211 can be breached in the same manner as the cassette membrane 210. Also, the variation depicted in FIG. 18 shows two streams of the pressurized gas 100 hitting the cassette membrane 210. In this variation, the two streams of the pressurized gas 100 can be created when the gas flow passageway 101 is split into two by the expansion chamber 10, the gas supply 4, or a combination thereof.

The pressurized gas 100 can deliver or propel the first-type particle 216a and the second-type particle 216b into the nozzle 12. The nozzle 12 can then be used to mix or combine the first-type particle 216a with the second-type particle 216b. In this variation, the delivery device 1 can deliver a mix of the first-type particle 216a and the second-type particle 216b to the treatment surface 11.

Also, in this variation, when the pressurized gas 100 has breached the portions of the cassette membranes 210 covering the upstream and downstream ends of the first particle reservoir 209*a* and the second particle reservoir 209*b*, the first particle reservoir 209*a* and the second particle reservoir 209*b* can become a part of the gas flow passageway 101.

FIGS. 19*a* and 19*b* illustrate that the particle cassette 200 can be designed or configured so that particles 216 of different types can be delivered or propelled to the treatment surface 11 in sequential order. As shown in FIG. 19*a*, the first particle reservoir 209*a* can be covered or sealed with a first membrane 210*a* and the second particle reservoir 209*b* can be covered or sealed with a second membrane 210*b*. The second membrane 210*b* can be composed or made of a different material composition or membrane thickness 207 than the first membrane 210*a*. For example, the second membrane 210*b* can be thicker than the first membrane 210*a* or be constructed of a higher molecular weight polymer than the first membrane 210*a*. As a more specific example, the first membrane 210*a* can be constructed or composed of PET and the second membrane 210*b* can be constructed or composed of polycarbonate.

FIG. 19*a* illustrates that the pressurized gas 100, when first released from the gas supply 4, can immediately create a membrane breach 218 in the first membrane 210*a* and propel the first-type particle 216*a* into the nozzle 12. FIG. 19*a* also illustrates that the second membrane 210*b* can initially withstand the force or pressure of the pressurized gas 100.

FIG. 19*b* illustrates that once the first-type particles 216*a* have exited the first particle reservoir 209*a*, the pressurized gas 100 can create a membrane breach 218 in the second membrane 210*b*. The pressurized gas 100 can then deliver or propel the second-type particles 216*b* into the nozzle 12. By covering the first particle reservoir 209*a* with a first membrane 210*a* and covering the second particle reservoir 209*b* with a second membrane 210*b*, the delivery device 1 can create a delay in delivering the second-type particle 216*b* to the treatment surface 11.

The delay can span several minutes, several seconds, or several milliseconds. Moreover, the delay can be adjusted by adjusting the thickness or material composition of the first membrane 210*a* relative to the second membrane 210*b*. When the pressurized gas 100 has created a membrane breach 218 in the first membrane 210*a* covering the upstream and downstream ends of the cassette housing 204, the first particle reservoir 209*a* can become part of the gas flow passageway 101. Similarly, when the pressurized gas 100 has created a membrane breach 218 in the second membrane 210*b* covering the upstream and downstream ends of the cassette housing 204, the second particle reservoir 209*b* can then become part of the gas flow passageway 101.

FIG. 20 illustrates that two particle cassettes 200 can be sequentially aligned along the device longitudinal axis 32. Although two particle cassettes 200 are shown in FIG. 20, it is contemplated that three, four, five, or more particle cassettes 200 can be aligned sequentially along the device longitudinal axis 32. One of the particle cassettes 200 can contain a different type of particles 216 or therapeutic agents than the other particle cassettes 200. The multiple particle cassettes 200 can be housed by the same expansion chamber 10 or different expansion chambers 10. The multiple particle cassettes 200 can be housed along different segments of the delivery device 1. The first particle reservoir 209*a* of one particle cassette 200 can contain the first-type particle 216*a* and the second particle reservoir 209*b* of the other particle cassette 200 can contain the second-type particle 216*b*. The first-type particle 216*a* can mix with the second-type particle 216*b* in the nozzle 12 or along the gas flow passageway 101.

In this disclosure "coupled" can mean, but is not limited to, physically connected or attached by a threading mechanism, interlocked, twisted, heat sealed, sealed, welded, sized to fit, clipped on, resting on or between, snap fit, interference fit, any combination thereof, or any other coupling mechanism known to one skilled in the art.

Each of the individual variations or embodiments described and illustrated herein has discrete components and features which may be readily separated from or combined with the features of any of the other variations or embodiments. Modifications may be made to adapt a particular situation, material, composition of matter, process, process act(s) or step(s) to the objective(s), spirit or scope of the present invention.

Methods recited herein may be carried out in any order of the recited events which is logically possible, as well as the recited order of events. Additional steps or operations may be provided or steps or operations may be eliminated to achieve the desired result.

Furthermore, where a range of values is provided, every intervening value between the upper and lower limit of that range and any other stated or intervening value in that stated range is encompassed within the invention. Also, any optional feature of the inventive variations described may be set forth and claimed independently, or in combination with any one or more of the features described herein.

All existing subject matter mentioned herein (e.g., publications, patents, patent applications and hardware) is incorporated by reference herein in its entirety except insofar as the subject matter may conflict with that of the present invention (in which case what is present herein shall prevail). The referenced items are provided solely for their disclosure prior to the filing date of the present application. Nothing herein is to be construed as an admission that the present invention is not entitled to antedate such material by virtue of prior invention.

Reference to a singular item, includes the possibility that there are plural of the same items present. More specifically, as used herein and in the appended claims, the singular forms "a," "an," "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise, all technical and scientific terms used herein have the same meaning as commonly understood by one of ordinary skill in the art to which this invention belongs.

This disclosure is not intended to be limited to the scope of the particular forms set forth, but is intended to cover alternatives, modifications, and equivalents of the variations or embodiments described herein. Further, the scope of the disclosure fully encompasses other variations or embodiments that may become obvious to those skilled in the art in view of this disclosure. The scope of the present invention is limited only by the appended claims.

I claim:

1. A device for delivering particles comprising:

a particle cassette comprising the particles, a cassette housing, and a cassette membrane, wherein the cassette housing comprises an Ethylene Vinyl Acetate (EVA) copolymer of 18% to 28% Vinyl Acetate (VA);

a gas supply configured to supply gas under pressure to deliver the particles by rupturing the cassette membrane; and wherein the cassette membrane is configured to cover the entire cassette housing.

2. The device of claim 1, wherein the cassette housing has a particle reservoir having an inner diameter from 5.0 mm to 7.0 mm.

3. The device of claim 1, wherein the cassette membrane comprises polycarbonate.

4. The device of claim 1, wherein the cassette membrane is 10 to 30 microns thick.

5. The device of claim 1, wherein the device comprises a trigger having a trigger proximal portion and a trigger distal portion and a disengageable safety interlock fixed to the case, wherein the disengageable safety interlock is configured to contact and impede actuation of the trigger distal portion when the disengageable safety interlock is engaged.

6. The device of claim 1, wherein the device comprises a silencer cover and a silencer packing material.

7. The device of claim 1, wherein the cassette housing comprises a male cassette part comprising a male threaded portion and a female cassette part comprising a female threaded portion, wherein the male cassette part is configured to be coupled to the female cassette part, and wherein a piece of the cassette membrane covers a male cassette port of the male cassette part and another piece of the cassette membrane covers a female cassette port of the female cassette part.

8. The device of claim 7, wherein the female cassette port extends from the female threaded portion, wherein the female cassette port has a port diameter and the female threaded portion has a female thread diameter, wherein the female thread diameter is greater than the port diameter.

9. The device of claim 1, wherein the cassette membrane further comprises at least one of polyethylene terephthalate and polyether ether ketone.

10. The device of claim 9, wherein the cassette membrane is composed of ⅓ polycarbonate, ⅓ polyethylene terephthalate, and ⅓ polyether ether ketone.

11. The device of claim 9, wherein the cassette membrane is composed of 50% polycarbonate and 50% polyether ether ketone.

12. The device of claim 9, wherein the cassette membrane is composed of 50% polycarbonate and 50% polyethylene terephthalate.

13. The device of claim 1, wherein the cassette membrane is configured to cover at least one port of the cassette housing and a portion of an outer radial wall of the cassette housing.

14. The device of claim 1, wherein the cassette membrane comprises a pre-perforated section configured to separate when the pressurized gas exceeds a burst pressure.

15. The device of claim 1, wherein the cassette housing comprises an upstream port and a downstream port, wherein the upstream port is covered by a first cassette membrane and the downstream port is covered by a second cassette membrane.

16. The device of claim 15, wherein the second cassette membrane is made of a different material than the first cassette membrane.

17. The device of claim 15, wherein the first cassette membrane has a first membrane thickness and the second cassette membrane has a second membrane thickness, and wherein the second membrane thickness is greater than the first membrane thickness.

18. A device for delivering particles comprising:
a particle cassette comprising the particles, a cassette housing, and a cassette membrane, wherein the cassette housing comprises an Ethylene Vinyl Acetate (EVA) copolymer of 18% to 20% Vinyl Acetate (VA);
a gas supply configured to supply gas under pressure to deliver the particles by rupturing the cassette membrane; and
wherein the cassette membrane is configured to cover the entire cassette housing.

19. A device for delivering particles comprising:
a particle cassette comprising the particles, a cassette housing, and a cassette membrane, wherein the cassette housing comprises an Ethylene Vinyl Acetate (EVA) copolymer of 18% Vinyl Acetate (VA);
a gas supply configured to supply gas under pressure to deliver the particles by rupturing the cassette membrane; and
wherein the cassette membrane is configured to cover the entire cassette housing.

* * * * *